US011795502B2

(12) United States Patent
Buersgens et al.

(10) Patent No.: US 11,795,502 B2
(45) Date of Patent: Oct. 24, 2023

(54) METHOD FOR MULTIPLYING NUCLEIC ACIDS

(71) Applicant: GNA Biosolutions GmbH, Planegg/Martinsried (DE)

(72) Inventors: Federico Buersgens, Planegg/Martinsried (DE); Joachim Stehr, Planegg/Martinsried (DE); Lars Ullerich, Planegg/Martinsried (DE); Cecilia Rebuffo-Scheer, Planegg-Martinsried (DE)

(73) Assignee: HP HEALTH SOLUTIONS GERMANY GMBH, Martinsried (DE)

( * ) Notice: Subject to any disclaimer, the term of this patent is extended or adjusted under 35 U.S.C. 154(b) by 6 days.

(21) Appl. No.: 16/599,754

(22) Filed: Oct. 11, 2019

(65) Prior Publication Data

US 2020/0109439 A1    Apr. 9, 2020

Related U.S. Application Data

(62) Division of application No. 15/525,217, filed as application No. PCT/EP2014/074210 on Nov. 10, 2014, now abandoned.

(51) Int. Cl.
| | |
|---|---|
| *C12P 19/34* | (2006.01) |
| *C12Q 1/686* | (2018.01) |
| *C12Q 1/6844* | (2018.01) |
| *C12Q 1/6848* | (2018.01) |
| *C12Q 1/6851* | (2018.01) |

(52) U.S. Cl.
CPC ........... *C12Q 1/686* (2013.01); *C12Q 1/6844* (2013.01); *C12Q 1/6848* (2013.01); *C12Q 1/6851* (2013.01)

(58) Field of Classification Search
CPC ..... C12Q 1/686; C12Q 1/6851; C12Q 1/6844
See application file for complete search history.

(56) References Cited

U.S. PATENT DOCUMENTS

| | | | |
|---|---|---|---|
| 4,683,202 | A | 7/1987 | Mullis |
| 7,998,672 | B2 | 8/2011 | Roper |
| 9,382,583 | B2 * | 7/2016 | Stehr ............... B01L 7/5255 |
| 9,926,594 | B2 * | 3/2018 | Stehr ............... B01L 7/5255 |
| 10,544,450 | B2 * | 1/2020 | Buersgens ........... C12Q 1/6844 |
| 2002/0055149 | A1 * | 5/2002 | Kopf-Sill ................. B01L 7/52 435/7.1 |
| 2002/0061588 | A1 | 5/2002 | Jacobson et al. |
| 2003/0143604 | A1 | 7/2003 | Storhoff et al. |
| 2010/0021973 | A1 | 1/2010 | Makarov et al. |
| 2010/0234579 | A1 | 9/2010 | Mirkin et al. |
| 2011/0262912 | A1 * | 10/2011 | Tomigahara ......... C12Q 1/6851 435/6.11 |
| 2013/0012399 | A1 | 1/2013 | Myers et al. |
| 2014/0377764 | A1 * | 12/2014 | Stehr ................ B82Y 20/00 435/6.12 |

FOREIGN PATENT DOCUMENTS

| | | | |
|---|---|---|---|
| DE | 102012201475 A1 * | 8/2013 | ............ B82Y 20/00 |
| DE | 102013215166 B3 | 10/2014 | |
| EP | 1842924 | 6/2009 | |
| EP | 2110175 A1 | 10/2009 | |
| WO | WO-2007/143034 A1 | 12/2007 | |
| WO | 2013/113965 | * 8/2013 | |

OTHER PUBLICATIONS

Dalmasso, A., et al., "Identification of Four Tuna Species by Means of Real-Time PCR and Melting Curve Analysis," (2007), Veterinary Research Communication, Suppl. 1, (pp. 355-357).
Scagliarini, A., et al., "TaqMan Based Real Time PCR for the Quanification of Canine Distemper Virus," (2007), Veterinary Research Communications, Suppl. 1, (pp. 261-263).
Murphy, J., et al., "Reliability of real-time reverse-transcription PCR iin clinical diagnostics: gold standard or substandard?," (2009), Expert Review of Mol. Diagn., (pp. 187-197).
Bellizzi, G., et al., "On the Energy Transfer Between the Electromagnetic Field and Nanomachines for Biological Applications," (2008), Bioelectromagnetics, (pp. 331-339).
Li, Min, et al., "Enhancing the efficiency of a PCR using gold nanoparticles," (2005), Nucleic Acids Research, vol. 33, No. 21, (pp. 10).
Govorov, A., et al., "Generating heat with metal nanoparticles," (2007), Nanotoday, vol. 2, No. 1, (pp. 30-38).
Hamad-Schifferli, Kimberly, et al.: "Remote electronic control of DNA hybridization through inductive coupling to an attached metal nanocrystal antenna", Jan. 10, 2002, Nature, vol. 415 (pp. 152-155).
Hanson, G. W., et al., "Electromagnetic absorption mechanism in metal nanospheres: Bulk and surface effects in radiofrequency-terahertz heating of nanoparticles," Journal of Applied Physics, 2011 (5 pgs.).

(Continued)

*Primary Examiner* — Kenneth R Horlick
(74) *Attorney, Agent, or Firm* — Foley & Lardner LLP

(57) ABSTRACT

One or more nanoparticles, each of which is conjugated with at least one oligonucleotide, are used to multiply nucleic acids. One or more of the oligonucleotides has at least one primer sequence and an additional segment extending from the end of the primer sequence proximal to the nanoparticle in the direction of the nanoparticle, and the additional segment has at least one abasic modification. The disclosed method for multiplying nucleic acids has a multiplication step and a test step for determining the concentration of the products of the multiplication reaction. The test step begins after the multiplication step ends, and in the test step, either at least one part of the sample is supplied with substances or no substances are supplied. In a method for multiplying nucleic acids, nanoparticles transfer heat into their surroundings in a reaction volume upon being excited. A method for multiplying a nucleic acid has an amplification step that uses a polymerase chain reaction, where a cycle consisting of the steps of denaturing, annealing, and elongating is repeated.

18 Claims, 11 Drawing Sheets

Specification includes a Sequence Listing.

(56) References Cited

OTHER PUBLICATIONS

Keblinski, Pawel, et al., "Limits of localized heating by electromagnetically excited nanoparticles", Journal of Applied Physics, 2006 (6 pgs.).

Li, Dongxiao, et al., "Negligible absorption of radiofrequency radiation by colloidal gold nanoparticles", Journal of Colloid and Interface Science, 2011 (pp. 47-53).

* cited by examiner

METHOD FOR MULTIPLYING NUCLEIC ACIDS

CROSS-REFERENCE TO RELATED APPLICATIONS

This application is a divisional of co-pending U.S. patent application Ser. No. 15/525,217, filed May 8, 2017, now abandoned, entitled METHOD FOR MULTIPLYING NUCLEIC ACIDS, which is a national stage application under 35 U.S.C. § 371 of PCT Application No. PCT/EP2014/074210, filed Nov. 10, 2014, which was published as WO 2016/074701 A1, which applications are incorporated herein by reference in their entirety.

DESCRIPTION

Field of the Invention

The invention relates to a method for the amplification of nucleic acids.

Background of the Invention

Methods for the amplification of nucleic acids are known from the prior art. The patent specification U.S. Pat. No. 4,683,202 discloses a method, with which at least one specific nucleic acid sequence contained in a nucleic acid or a mixture of nucleic acids can be amplified, wherein each nucleic acid consists of two separate, complementary strands, of equal or unequal length. The method comprises: (a) treating the strands with two primers for each different specific sequence being amplified under such conditions that, for each different sequence being amplified, an extension product for each primer is synthesized, which is complementary to the respective nucleic acid strand. Said primers are selected so that they are substantially complementary to different strands of each specific sequence, so that the extension product that is synthesized from a primer can be used, if separated from its complement, as a template for the synthesis of the extension product of the other primer; (b) separating the primer extension products from the templates, on which they were synthesized so that single-stranded molecules are produced; (c) treating the single-stranded molecules from step (b) with the primers from step (a) under such conditions that a primer extension product is synthesized, wherein each of the single strands of step (b) is used as a template. The steps can be carried out one after the other or simultaneously. In addition the steps (b) and (c) can be repeated until the desired degree of sequence amplification is achieved. If in the method the steps (a) and (c) are carried out with the aid of a polymerase the method is usually referred to as a polymerase chain reaction (PCR).

In the international application laid open for public inspection WO 2007/143034 A1, methods are disclosed that are to be suitable for performing a PCR. The methods may include the use of an optical radiation source for heating in a PCR. The methods may also include the use of surface plasmon resonance or fluorescence resonance energy transfer for monitoring a PCR in real-time. The methods may further include the immobilization of a template, primer or a polymerase on a surface such as gold or another surface that is active in relation to the surface plasmon resonance.

The patent application US 2002/0061588 A1 discloses methods for making nucleic acids locally and directly responsive to an external signal. The signal acts only on one or a plurality of specific localized portions of the nucleic acid. According to the invention the signal can change the properties of a specific nucleic acid and thereby also change its function. Accordingly the invention provides methods for regulating the structure and functioning of a nucleic acid in a biological sample without influencing other constituent parts of the sample. In one embodiment a modulator transfers heat to a nucleic acid or a part of a nucleic acid, which results e.g. in intermolecular or intramolecular bonds being destabilized, and the structure and stability of the nucleic acid changing. Preferred modulators include metal nanoparticles, semiconductor nanoparticles, magnetic nanoparticles, oxide nanoparticles and chromophores. It is also proposed to use these methods in association with a PCR. It is proposed in particular to control a PCR reaction with a modulator.

The patent application US 2003/0143604 A1 relates to the use of nanoparticle detection probes for monitoring amplification reactions, in particular PCR. The patent application deals primarily with the use of nanoparticle-oligonucleotide conjugates which are treated with a protective reagent such as bovine serum albumen, in order to detect a target polynucleotide quantitatively and qualitatively. The patent application discloses a nucleic acid amplification and detection using gold nanoparticle primers. In a first step the nucleic acid target is denatured in the presence of the gold nanoparticles, to which primers are attached. In a second step the gold nanoparticles hybridize with the primers attached thereto to the nucleic acid target and a copy of the complementary DNA sequence is produced based on the nucleic acid primers which are attached to the nanoparticles. The first and second steps are repeated and the optical signal which is produced through the binding of complementary nanoparticle probes that have been amplified is measured.

The patent application DE 10 2012 201 475 A1 relates to a method for the amplification of nucleic acids. In this method, nanoparticles in a reaction volume transfer heat to their environment through excitation.

The patent DE 10 2013 215 B3 (publication date of the grant of patent: 30 Oct. 2014) of the inventors of this patent application contains a method for super-amplification using nanoparticles which are each conjugated to at least one oligonucleotide. In the method, the shortening of the cycle duration leads to a low yield per cycle, but which is more than compensated by the possibility of being able to perform more cycles per time unit. The oligonucleotide(s) has/have at least one primer sequence and a further portion which extends from the nanoparticle-proximal end of the primer sequence in the direction of the nanoparticle, wherein the further portion has at least one abasic modification.

OBJECT OF THE INVENTION

It is the object of the invention to provide an improved use of one or a plurality of nanoparticles, which are each conjugated to at least one oligonucleotide, for the amplification of nucleic acids. It is further the object of the invention to provide an improved method for the amplification of nucleic acids.

SOLUTION ACCORDING TO THE INVENTION

In one aspect of the invention the object of the invention is accomplished by using one or a plurality of nanoparticles, which are each conjugated to at least one oligonucleotide, for the amplification of nucleic acids, wherein one or a plurality of the oligonucleotides have at least one primer sequence and a further portion, which extends from the nanoparticle-proximal end of the primer sequence in the direction of the nanoparticle, and wherein the further portion has at least one abasic modification.

It is an achievable advantage of this embodiment of the invention that, in the case of the primer sequence serving, typically but not necessarily after its elongation, as a template for the synthesis of a complementary strand by means of a DNA polymerase, an activity of the polymerase beyond the abasic modification is prevented in part or even completely. In other words it is possible to avoid a part of the portion located, as seen from the primer sequence, beyond the abasic modification being used by the DNA polymerase as a template for the synthesis of a complementary strand.

Consequently, through this embodiment of the invention an unnecessary length of the synthesis product can be counteracted. Problems can thereby be counteracted, e.g., which are due to an unnecessarily long complementary strand requiring a higher melt temperature for the de-hybridization of the oligonucleotides conjugated to the nanoparticle. Also, problems can be counteracted, for example, that arise through the unnecessarily long complementary strand being unnecessarily non-specifically hybridized in subsequent hybridization steps and the specificity of the amplification method thereby being impaired.

The nanoparticles according to the invention are preferably particles which, due to their size, have particular optical properties, e.g. characteristic absorption or scattering spectra, which do not emerge, or do not emerge so clearly, in the volume material. The nanoparticles preferably have a diameter of between 2 and 500 nm, particularly preferably between 3 and 300 nm and more particularly preferably between 5 and 200 nm. Preferred nanoparticles have a diameter of between 7 and 150 nm. The nanoparticles can be spherical, but in particular also non-globular forms, e.g. elongated nanoparticles (nanorods), can also be considered. In a preferred embodiment of the invention the nanoparticle comprises at least one semiconductor or a metal, preferably a precious metal, e.g. gold or silver. In one embodiment the nanoparticle consists completely of the metal, in another embodiment the metal forms only a part of the nanoparticle, e.g. its shell. A preferred nanoparticle may be a shell core-shell nanoparticle. A preferred nanoparticle may have pores at its surface, which may be occupied by atoms or molecules with a size and charge determined by the properties of the pores. These atoms or molecules particularly preferably attach themselves to the nanoparticle only when it is in a solution. According to the invention the nanoparticle also comprises the atoms and molecules taken up at its surface. Preferred nanoparticles are suited, due to their material absorption or plasmon resonance, for absorbing optical energy.

The term "oligonucleotide" includes within the sense of the present invention not only (desoxy) oligoribonucleotides, but also oligonucleotides that contain one or more nucleotide analogues with modifications on their backbone (e.g. methylphosphonates, phosphorothioates or peptic nucleic acids (PNA), in particular on a sugar of the backbone (e.g. 2'-O-alkyl derivatives, 3'- and/or 5'-aminoriboses, locked nucleic acids (LNA), hexitol nucleic acids, morpholinos, glycol nucleic acid (GNA), threose nucleic acid (TNA) or tricyclo-DNA—see in this combination the dissertation by D. Renneberg and C. J. Leumann, "Watson-Crick base-pairing properties of Tricyclo-DNA", J. Am. Chem. Soc., 2002, Volume 124, pages 5993-6002, of which the related content is part of the present disclosure through reference thereto) or that contain base analogues, e.g. 7-deazapurine or universal bases such as nitroindole or modified natural bases such as N4-ethyl-cytosine. In one embodiment of the invention the oligonucleotides are conjugates or chimera with non-nucleoside analogues, e.g. PNA. The oligonucleotides contain in one embodiment of the invention, at one or more positions, non-nucleoside units such as spacers, e.g. hexa-ethylene glycol or $C_n$-spacers with n between 3 and 6. If the oligonucleotides contain modifications these are selected so that, also with the modification, hybridization with natural DNA/RNA analytes is possible. Preferred modifications influence the melt behaviour, preferably the melt temperature, in particular in order to be able to differentiate hybrids with different degrees of complementarity of their bases (mismatch discrimination). Preferred modifications include LNA, 8-aza-7-deazapurine, 5-propinyl-uracil and cytosine and/or abasic interruptions or modifications in the oligonucleotide. Further modifications in the sense of the invention are, e.g., modifications with biotin, thiol and fluorescence donor and fluorescence acceptor molecules.

An abasic modification in the sense of the present invention is a portion of the oligonucleotide, in which the sequence of nucleotides is interrupted by the introduction of one or more molecules that do not constitute nucleotides, in such a way that a polymerase completely or partially interrupts the synthesis of an otherwise completely or partially hybridized, complementary oligonucleotide with respect to this portion, as there is insufficient base complementarity on this portion.

In a further aspect of the invention the object of the invention is achieved by means of a method for the amplification of nucleic acids in a sample, wherein the method includes an amplification step to amplify the nucleic acids and a test step to determine the concentration of the products of the amplification step, wherein the test step begins after the end of the amplification step, and wherein substances are added to the sample or a part of the sample in the test step. This also includes cases in which the sample or a part of the sample is added to another preparation, e.g. a test preparation containing test probes.

It is an achievable advantage of this embodiment of the invention that the amplification step and the test step can take place under different reaction conditions. Further reaction partners which improve the reaction conditions for the test step, e.g. a salt, a buffer or a detergent, can advantageously be added only after conclusion of the amplification step. It is advantageously possible to avoid having to make a compromise, with the substances located in the sample, between the requirements of the amplification step and the test step.

An amplification step in the sense of the present invention is a step of the method according to the invention, in which nucleic acids present in the sample are amplified. The amplification step can have several sub-steps, in each of which amplification takes place. For example such a sub-step can be passing through, i.e. the passage of, an amplification cycle, as typically repeatedly passed through in a polymerase chain reaction (PCR). It is possible for a further amplification step to follow the test step which follows the amplification step. The method can therefore include one or more amplification steps.

A test step in the sense of the present invention is a step of the method according to the invention, in which the concentration of the products of the amplification step is determined. This can also take place in a plurality of sub-steps. It is possible for the test step to be followed by a further amplification step, which is followed by a further test step, so that there are two test steps. The method can therefore include one or more test steps. The alternating sequence of amplification and test steps can be continued, so that the method includes many amplification steps and many test steps.

In a further aspect of the invention the object of the invention is achieved by means of a method for the amplification of nucleic acids in a sample, wherein the method includes an amplification step to amplify the nucleic acids and a test step to determine the concentration of the products of the amplification step and wherein no substances are added to the sample in the test step. The test step can thereby follow the amplification step or overlap with the amplification step means of, also completely overlap it.

It can advantageously be achieved with this embodiment of the invention that the test step takes place, without further work steps and without further time loss, already during the amplification reaction or directly after the amplification reaction. Reaction partners that improve the reaction conditions for the test step, e.g. a salt, a buffer or a detergent, are advantageously already contained in the reaction volume during the amplification reaction in this embodiment of the invention.

In a further aspect of the invention the object of the invention is achieved by means of a method for the amplification of nucleic acids, wherein nanoparticles in a reaction volume transfer heat to their environment through excitation.

Known methods for the amplification of nucleic acids contain one or a plurality of steps, in which at least parts of the sample must be heated. It can be achieved through the invention that, in the method for the amplification of nucleic acids, it is not necessary to heat the whole reaction volume. It is possible on the other hand to heat only specific parts of the reaction volume through excitation of nanoparticles. It is advantageously possible to heat only those parts of the reaction volume that must be heated for the amplification of the nucleic acids. In this way heat-sensitive constituent parts of the sample can be protected. Local heating may be quicker than global heating of the whole reaction volume if less energy has to be transferred. It is thus advantageously possible through the invention to provide a method for the amplification of nucleic acids that is quicker and requires less energy.

The method according to the invention takes place in a chamber which is referred to below as the reaction volume. The reaction volume can be enclosed by a reaction vessel. The reaction volume contains a sample, in which usually the nucleic acid(s) to be amplified is/are present. The sample can include a liquid, preferably water. The liquid can advantageously serve as a suspension medium and/or solvent for the originals and complements and/or other constituent parts of the sample.

If, through excitation of a nanoparticle, heat is transferred to its environment, this means according to the invention that energy is transferred to the nanoparticle, wherein the nanoparticle heats its environment through the transfer of the energy. Through the excitation of the nanoparticles, the direct environment of the nanoparticles is preferably heated more than the more distant environment of the nanoparticles. Usually the nanoparticles are initially heated by excitation and then transfer heat to their environment. However, it is also conceivable that, through the excitation of the nanoparticles, heat is transferred to their environment without the nanoparticles firstly being heated themselves. The environment of the nanoparticles is preferably a spherical volume which has 100 times (100×) the diameter of the nanoparticle located at its centre point, particularly preferably 10× the diameter, more particularly preferably 4× the diameter and preferably less than 2× the diameter.

In a further aspect of the invention the object of the invention is achieved by means of a method for the amplification of nucleic acids by means of a polymerase chain reaction (PCR), wherein a cycle consisting of the steps: denaturing, annealing and elongation is repeatedly carried out.

If at least two steps of the PCR are performed at different temperatures, it may be necessary to provide one or more heating steps and/or cooling steps in the cycle, in which the reaction volume or parts of the reaction volume are heated or cooled. A heating or cooling step can take place before or after one of the steps of denaturing, annealing and elongation. A heating or cooling step thereby typically overlaps with the preceding and/or the subsequent denaturing, annealing or elongation step. The heating is preferably achieved in the heating step, or in at least one of the heating steps, at least in part through excitation of the nanoparticles and is preferably local heating.

In a PCR a cycle including the steps denaturing, annealing (also referred to as hybridization) and elongation is repeatedly passed through and preferably in this sequence. In addition it is preferable for each of these steps to be of equal length in all passages of the cycle. This is, however, by no means necessary. One or more of the steps in one passage of the cycle can, by all means, have a shorter duration than in other passages of the cycle. The duration $t_c$ of a passage of the cycle is referred to below as a cycle duration.

A nucleic acid to be amplified is referred to below as an original. Another common term is "amplicon". The original is a single strand and can form, in the reaction volume, together with its complementary strand, which is described as a complement, a double strand. After each passage of the cycle a copy produced of the original is an original for the next passage of the cycle and a copy produced of the complement is a complement for the next passage of the cycle. In a passage of the cycle the number of specimens of the original and complement can be increased. The cycles of the method according to the invention are passed through at least in a part of the sample.

The denaturing step serves to denature a nucleic acid double strand, i.e. to separate it into its two single strands. For example, the original can be separated from the complement in the denaturing step. Denaturing is also referred to as melting. The denaturing of the nucleic acid double strand is usually thermally induced, i.e. at least a part of the nucleic acid double strand or the whole double strand is exposed to a temperature, described as a denaturing temperature, which causes or at least encourages a separation of the nucleic acid double strands. The denaturing temperature does not have to be a fixed temperature but can also be a temperature interval, within which the temperature in the denaturing step varies. The preferred denaturing temperature is selected on the one hand to be so high that nucleic acid double strands can be separated. On the other hand the preferred denaturing temperature is selected to be so low that a DNA polymerase, which is possibly also located in the sample, is not substantially damaged. A typical value for the denaturing temperature is 95° C.

The reaction volume further contains preferably at least one, particularly preferably at least two oligonucleotides, which are described as primers. One of these primers is described as a forward primer and another as a reverse primer. The forward primer is complementary to the 3'-end of the original. The reverse primer is complementary to the 3'-end of the complement. Annealing is understood to be the hybridization of the forward primers with the original and the reverse primers with the complement. The annealing step serves for the hybridization of the forward and reverse primers to their complementary sequences in the original or complement. The annealing is also usually thermally induced, i.e. at least a part of the original or the complement, or the whole original or the whole complement, is exposed to a temperature which is described as the annealing temperature, which causes or at least encourages a hybridization of the forward and reverse primers to their complementary sequences in the original or complement. Like the denaturing temperature, the annealing temperature can also be a temperature range, within which the temperature varies in the annealing step. The annealing step typically takes place at temperatures of 50° C. to 65° C. The annealing temperature is selected so that a hybridization of the primers that is as specific as possible can take place.

Hybridization means in the sense of the present invention the formation of a double strand from two single strands, which can each consist of a nucleic acid and/or an oligonucleotide. Under suitable reaction conditions the hybridization generally leads to the lowest possible energy state that can be achieved by the combination of the two single strands. In other words, under suitable conditions, the two single strands preferably bind to each other in such a way that, with respect to the sequences of the two single strands, the greatest possible complementarity (e.g. specificity) is produced. If a nucleic acid A is partially complementary to a nucleic acid B, this means that the nucleic acid A is complementary in one part to a part of the nucleic acid B.

The reaction volume further contains preferably a DNA polymerase. The DNA polymerase can synthesize, in an elongation step starting from the forward primer, a copy of the complement. Starting from the reverse primer the DNA polymerase can synthesize a copy of the original. Through the synthesis the copy of the complement is hybridized with the original and the copy of the original is hybridized with the complement. For the purpose of elongation the DNA polymerase is exposed to a temperature, described as the elongation temperature, which allows or at least encourages an elongation. The elongation temperature can also be a temperature range, within which the temperature varies in the elongation step. When using a polymerase of *Thermus aquaticus* (Taq), an elongation temperature of 72° C. is typically used. In some embodiments of the PCR the annealing temperature and the elongation temperature are identical, i.e. both steps take place at the same temperature.

PREFERRED EMBODIMENTS OF THE INVENTION

Advantageous embodiments and refinements, which can be used individually or in combination with each other, are the subject matter of the dependent claims.

It is preferable with the invention to amplify in particular nucleic acids that originate from organisms, including viruses, and can accordingly include for example genomic DNA, organelle DNA, plasmid DNA, RNA and mRNA.

The invention is particularly well suited for the amplification of nucleic acids that are shorter than 150 bases, particularly preferably shorter than 100 bases, particularly preferably shorter than 80 bases, particularly preferably shorter than 60 bases.

In a preferred embodiment of the invention the nanoparticles are conjugated to oligonucleotides. The nanoparticles form in this way nanoparticle-oligonucleotide conjugates. It can therefore advantageously be achieved that the oligonucleotides are specifically heated through excitation of the nanoparticles without the whole reaction volume having to be heated. In a particularly preferred embodiment the nanoparticles are conjugated to primers. More particularly preferably the nanoparticles are conjugated to the forward and reverse primers of the PCR. In a preferred embodiment of the invention, forward primers, but no reverse primers, are attached to one class of nanoparticle-oligonucleotide conjugates, and reverse primers, but no forward primers, are attached to a different class.

In a further preferred embodiment a class of conjugates of nanoparticles and oligonucleotides is conjugated both with forward and also reverse primers. In this embodiment, in a PCR, starting from the forward primer on a nanoparticle, a new DNA single strand complementary to the original is written. This new DNA single strand is conjugated to the nanoparticle, as the new DNA single strand contains the forward primer. Directly after writing, the new DNA single strand forms, with the original, a double-stranded. In a subsequent denaturing step the new DNA single strand is separated from the original. At an annealing temperature the new DNA single strand hybridizes with a reverse primer, which is located on the surface of the nanoparticle, so that a loop is produced. For hybridization with the reverse primer of the same nanoparticle, only a short distance must be covered. For hybridization with a reverse primer on a different nanoparticle, a longer distance must be covered on average with preferred concentrations of nanoparticles. It can thus be advantageously achieved in this embodiment that the annealing takes place more quickly and a PCR can be performed more quickly.

In a preferred embodiment the heat transferred through the excitation of the nanoparticles to their environment is sufficient in order to de-hybridize the oligonucleotides on the surface of the nanoparticles from nucleic acids hybridized with the oligonucleotides. In this embodiment nanoparticles are conjugated to oligonucleotides and at least some of these oligonucleotides are hybridized with at least partially complementary nucleic acids. Through the excitation of the nanoparticles, thermal energy is transferred to the surrounding water and the temperature of the water around the nanoparticles therefore preferably suffices in order to denature the oligonucleotides from the nucleic acids combined with them.

In the present invention, preferably one or more nanoparticles, which are each conjugated to at least one oligonucleotide, are used for the amplification of nucleic acids, wherein one or more of the oligonucleotides has/have at least one primer sequence and a further portion, which extends from the nanoparticle-proximal end of the primer sequence in the direction of the nanoparticle, and wherein the further portion has at least one abasic modification.

The preferred abasic modification is arranged at the end, facing towards the primer sequence, of the further portion adjacently to the primer sequence. Through this embodiment of the invention an elongation of a complementary strand beyond the primer can be partially or even completely prevented.

The preferred abasic modification is arranged in a 3'-sided manner with respect to the primer sequence. With this embodiment of the invention an elongation of the primer sequence in 3'-direction beyond the abasic modification is advantageously prevented partially or even completely.

The abasic modification is preferably selected from the group including: 1',2'-dideoxy-ribose (dSpacer), triethylene glycol (Spacer9) and hexaethylene glycol (Spacer18).

Insofar as the further portion has a plurality of abasic modifications, these are preferably arranged directly adjacently to each other. If the further portion has a plurality of abasic modifications, each abasic modification is preferably selected form the group 1',2'-dideoxy-ribose, triethylene glycol and hexaethylene glycol.

The further portion preferably has at least, inter alia, the function of a spacer (hereinafter also referred to as a spacer sequence) that produces a distance or space between the primer sequence and the nanoparticle or enlarges such a space or distance. In other words, the spacer sequence serves as a spacer for the rest of the oligonucleotide. Due to the fact that the primer sequence is spaced further apart from the nanoparticles by the spacer sequence, the nucleic acids to be amplified and the DNA polymerases can advantageously find a better access to the primer sequences. In a preferred embodiment, after being synthesized, the copies of the original and of the complement remain fixed via the spacer sequence on the surface of the nanoparticles. In a particularly preferred embodiment the spacer sequence has a detection sequence of a restriction endonuclease, such that the synthesized copies can be cut off from the nanoparticles. This preferably takes place after the amplification has been completed, but can also take place during the amplification. It is thus possible with the invention to produce copies of nucleic acids that are present freely in the sample.

In a preferred embodiment of the invention, filling molecules are applied to the nanoparticles. The filling molecules prevent the undesired aggregation of the nanoparticles in the sample. The filling molecules thus advantageously serve to stabilize the nanoparticles. The charge of the nanoparticles can be modulated through the filling molecules. It is hereby possible to adapt the salt concentration found in the environment of the nanoparticles so that the DNA polymerase can synthesize as quickly as possible and the method can be performed advantageously quickly. The filling molecules can consist of oligonucleotides, but which are not primers and are preferably shorter than the primers. The filling molecules can also consist, e.g., of polymers, such as e.g. polyethylene glycol. In a preferred embodiment, the filling molecules allow the number of primers on the nanoparticles to be reduced, and instead to use more filling sequences, without causing significant efficiency losses in the method. In a preferred embodiment of the method the spacer sequences are at least just as long as the filling molecules. In this way it is advantageously possible to avoid the primer sequences being concealed by the filling molecules.

In a preferred embodiment of the invention the nanoparticles are combined with the oligonucleotides such that covalent bonds with more than one thiol are present between oligonucleotides and nanoparticles. PCR buffers generally contain dithiothreitol, which destabilizes the thiol bond between a gold nanoparticle and an oligonucleotide and which can lead, in particular with thermal loading such as e.g. during the denaturing, to oligonucleotides detaching from the nanoparticles. Covalent bonds with more than one thiol between oligonucleotide and nanoparticle can reduce the detachment of the oligonucleotides and thus increase the efficiency of the PCR.

In an embodiment of the present invention the amplification of nucleic acids in a sample includes an amplification step to amplify the nucleic acids and a test step to determine the concentration of the products of the amplification step, wherein the test step begins after the end of the amplification step and wherein substances are added to the sample in the test step.

In another embodiment of the present invention the method for the amplification of nucleic acids includes an amplification step to amplify the nucleic acids and a test step to determine the concentration of the products of the amplification step, wherein no substances are added to the sample in the test step. The test step can thereby follow the amplification step or overlap with the amplification step, also completely overlap with it. Preferably the salt conditions and/or the buffer, particularly preferably all chemical reaction conditions, are equal in the amplification step and in the test step.

In a preferred embodiment of the invention a global temperature of the sample during the test step is different from a global temperature of the amplification step. In other words, at least at one point in time of the test step, the global temperature of the sample is different from the global temperature of the sample at least at one point time of the amplification step. Particularly preferably a global temperature of the sample during the test step, particularly preferably at the start of the test step, particularly preferably during the predominant time of the test step, particularly preferably during the whole test step, is different from a global temperature during the amplification step, particularly preferably at the end of the amplification step, particularly preferably during the predominant time of the amplification step, particularly preferably during the whole amplification step.

It is an achievable advantage of this embodiment of the invention that the amplification step and the test step can take place under different reaction conditions. It is advantageously possible to avoid a compromise having to be made, with the global temperature, between the requirements of the amplification step and the test step.

In the sense of the present invention the global temperature is the average temperature of the sample, at which the amplification step and the test step are carried out. In the sense of the present invention the "predominant" part of the time of a step means more than 50% of the duration of this step.

In one embodiment of the invention "different from" is especially "higher than", in another embodiment especially "lower than". In a preferred embodiment "different" means that the temperatures differ by more than 1 degree, particularly preferably more than 2 degrees, particularly preferably more than 5 degrees, particularly preferably more than 10 degrees, particularly preferably more than 20 degrees, particularly preferably more than 40 degrees.

In a preferred embodiment of the invention a global temperature of the sample during the test step is substantially equal to a global temperature of the amplification step. In order words, at least at one point in time of the test step the global temperature of the sample is substantially equal to the global temperature of the sample at least at one point in time of the amplification step. Particularly preferably a global temperature of the sample during the test step, particularly preferably at the start of the test step, particularly preferably during the predominant time of the test step, particularly preferably during the whole test step, is substantially equal to a global temperature during the amplification step, particularly preferably at the end of the amplification step, particularly preferably during the predominant time of the amplification step, particularly preferably during the whole amplification step.

In a preferred embodiment "equal" means that the temperatures differ by less than 20 degrees, particularly preferably less than 10 degrees, particularly preferably less than 5 degrees, particularly, particularly preferably less than 2 degrees, particularly preferably less than 1 degree.

In the test step for determining the concentration of the products of the amplification step, test probes are preferably used that have a nanoparticle. The test probes are fed to the sample in one embodiment of the invention in the test step. In another embodiment of the invention, the test probes are fed to the sample before the test step, preferably before or during the amplification step.

In a preferred embodiment of the method the oligonucleotides on the nanoparticles of the test probes have a spacer sequence as a sub-sequence. The spacer sequence is thereby on the side, facing towards the nanoparticle, of the respective oligonucleotide. The spacer sequence thus serves as a spacer for the rest of the oligonucleotide. In a preferred embodiment an oligonucleotide contains both a sub-sequence that is described as a test sequence and also a sub-sequence that is a spacer sequence. In a preferred embodiment filling molecules are applied to the nanoparticles. The test sequences can hybridize with products of the amplification reaction. The test sequences are thereby preferably complementary to the products of the amplification reaction.

In a preferred embodiment the test sequences have, at the 3' end, one or more terminating modifications, such as e.g. dideoxy cytidine (ddC). These modifications can advantageously prevent the 3' extension of the test sequence through the polymerase and thus prevent the test sequences also being able to serve as primers.

In a preferred embodiment of the invention, nanoparticles which serve for the amplification (hereinafter also referred to as first nanoparticles in order to differentiate them from the nanoparticles of the test probes, hereinafter also referred to as second nanoparticles) are conjugated to forward primers. In the presence of the original and a DNA polymerase the forward primers are extended so that complements are produced, which are bonded via the forward primers to the first nanoparticles. A complement consists of the forward primer and an extension sequence, which arises through the extension of the forward primer. In an optional intermediate step, the originals are denatured from the complements through local or global heating. The first nanoparticles are then brought together with test probes if this has not already taken place. The test sequences of the test probes are complementary to the extension sequences so that the test probes can bind via test sequences to the extended forward primers on the first nanoparticles. Under suitable reaction conditions the combination of the first nanoparticles with the test probes comes about to the extent in which nanoparticle-bound complements are also present. This means that, if no extension sequences are produced, no combination of test probes and first nanoparticles arises. The reaction conditions of the amplification according to the invention and the detection through test probes are particularly preferably selected so that the extent of the combination of first nanoparticles with test probes allows conclusions to be drawn concerning the concentration of the original that was present in the sample before the amplification. Through the combination of the first nanoparticles with the test probes a measureable change can arise, e.g. a redshift or broadening of the plasmon resonance in the extinction spectrum. In a quite particularly preferred embodiment the measurable change that arises through the combination of test probes and first nanoparticles is proportional to the concentration of the original in the sample before the amplification. Concentration detection can thus advantageously be realized with simple means.

In a further preferred embodiment the method includes forward primers, which are conjugated to first nanoparticles, and free, thus non-nanoparticle-bound, reverse primers. In a first step the forward primers are extended in the presence of the original through a DNA polymerase to nanoparticle-bound complements. In a second step, starting from the free reverse primer, which binds to the nanoparticle-bound complement, a copy of the original is synthesized. Subsequently the first nanoparticles are brought together with test probes if this has not already taken place. The test sequences in this embodiment are complementary to the forward primers. If the forward primers have not been extended, the test probes can bind well to the first nanoparticles. If the forward primers have been extended, the binding of test sequences to forward primers is hindered by steric obstacles. If a newly synthesized copy of the original is hybridized with the extended forward primer, the binding of the test sequence to the extended forward primer is prevented. In this way the degree of combination between first nanoparticles and test probes decreases to the same extent as that in which products of the amplification reaction, i.e. complements and copies of the original, were synthesized. With a suitable selection of the reaction conditions a concentration detection of the original in the sample can be carried out, such that a measurable change is lower, the more original that was present in the sample before the amplification. The measurable change can thereby be, e.g., a redshift or broadening of the plasmon resonance in the extinction spectrum. A simple test can advantageously be designed which allows the determination of concentrations of specific nucleic acids.

In a further preferred embodiment the reverse primers are also conjugated to nanoparticles. In a particularly preferred embodiment the reverse primers are also conjugated to the first nanoparticles, which are also conjugated to the forward primers.

The nanoparticles of the test probes preferably have a different size from the nanoparticles used in the amplification step to amplify the nucleic acids. The nanoparticles of the test probes are particularly preferably smaller than the nanoparticles used in the amplification step to amplify the nucleic acids. The volume of the nanoparticles of the test probes is particularly preferably less than 50%, particularly preferably less than 25%, particularly preferably less than 12.5%, particularly preferably less than 6%, particularly preferably less than 3%, particularly preferably less than 1%, particularly preferably less than 0.1%, of the volume of the nanoparticles used in the amplification step to amplify the nucleic acids.

Through this embodiment of the invention a different local temperature can be reached around the nanoparticles of the test probes during the amplification reaction from that reached around the nanoparticles used to amplify the nucleic acids. For example, with test probes that are smaller than the nanoparticles used to amplify the nucleic acids, it can be achieved that the first nanoparticles reach a sufficient temperature for the amplification reaction, but the test probes reach a lower temperature. In this way it can be achieved that the test probes are thermally loaded less. It can also be achieved that no amplification reaction can take place on the test probes. The latter is advantageous particularly in embodiments of the invention, in which the test probes are located in the sample during the amplification reaction.

In one embodiment of the invention nanoparticles in a reaction volume transfer heat to their environment through excitation.

Through the excitation of the nanoparticles the environment of the nanoparticles is preferably locally heated, as particularly rapid temperature changes are possible especially when the heated volume only accounts for a small fraction of the total volume. On the one hand, with just a small energy input through irradiation, a high temperature difference can already be produced. On the other hand, a very rapid cooling of the heated volume is possible if a sufficiently large cold temperature tank is present in the irradiated volume in order to cool the nanoparticles and their environment again after the irradiation. This can be achieved by the nanoparticles being irradiated sufficiently greatly (in order to reach the desired temperature increase) and sufficiently shortly (in order that the heat remains localized). In the case of the amplification being carried out by means of a polymerase, e.g. a DNA polymerase, it is possible through the local heating to expose the polymerases to a lower heat.

A local heating in the sense of the present invention is present if the duration of the excitation in the respectively irradiated volume (e.g. in the laser focus) t is selected to be shorter than, or comparably short to, a critical excitation duration t1. t1 is determined by the time required by the heat to diffuse, with an average nanoparticle distance, from one nanoparticle to the next, multiplied by a scaling factor s1. In the case of an average nanoparticle distance $|x|$ and a temperature conductivity D of the medium between the nanoparticles t1 given by $t1=(s1\cdot|x|)^2/D$, wherein the temperature conductivity D typically in an aqueous solution has a value of $D=10^{-7}$ m$^2$/s.

The scaling factor s1 is a measure of how far the heat front of a particle spreads during the excitation duration. The temperature increase through an excited nanoparticle at a distance of a few nanoparticle diameters is only a very small fraction of the maximum temperature increase on the particle surface. In one embodiment of the invention an overlap of the heat fronts of a few nanoparticles is allowed in the sense that, in order to define the critical excitation duration t1 using the abovementioned formula, a scaling factor s1 of greater than 1 is used. In another embodiment of the invention, no overlap of the heat fronts is allowed during the excitation duration (corresponding to a greatly localized heating) in the sense that, in order to define the critical excitation duration t1 using the abovementioned formula, a scaling factor s1 of less than or equal to 1 is used. To define the local heating, preferably s1=100, preferably s1=30, preferably s1=10, preferably s1=7, preferably s1=3 and more particularly preferably s1=1, preferably s1=0.7, preferably s1=0.3.

Values for s1>1 can be advantageous, inter alia, for example in such cases in which the irradiated volume has a high aspect ratio (for example in the focus of a moderately focused laser beam), so that there is a comparably high number of nanoparticles located on the surface of the irradiated volume, and fewer heated nanoparticles are therefore located in their environment, and a great heat removal from the irradiated volume takes place, so that the heating contribution of the more remote neighbours remains negligible for longer.

This means that; for example in the case of a nanoparticle concentration of 1 nM, there is an average nanoparticle distance of $|x|=1.2$ micrometres, so that a local heating according to the invention is present, insofar as the excitation duration is less than t1=14 microseconds (the scaling factor is selected here as s1=1).

It is to be assumed that if t>t1 is selected, the heat emitted by the nanoparticles can consequently cover, through diffusion, during the irradiation, a distance that is greater than the average nanoparticle distance and this leads as a result to a superimposition of the heat fronts of many nanoparticles so that a temperature increase takes place in the whole volume between the nanoparticles. The temperature increase should be spatially more homogeneous in the irradiated volume, the longer it is heated, as not only the contributions of the closest nanoparticles but also of more remote neighbours are included in the temperature distribution around a nanoparticle. If the reaction volume is irradiated with a radiation absorbed by the nanoparticles for longer than t1, the heating is therefore described as global.

A global heating according to the invention can also take place, e.g., in that the reaction volume is heated from externally with a Peltier element or a resistance heater. The global heating can also be carried out in that, e.g. the reaction volume is irradiated with a radiation that is absorbed by the water in the sample more greatly than, or similarly greatly to, its absorption by the nanoparticles.

"Temperature increase" hereby means the difference between the temperature at a location at the observation time directly after the excitation and the temperature at the same location at the time directly before the excitation. Global heating and local heating can also be carried out simultaneously.

The excitation of the nanoparticles preferably takes place through an alternating field, particularly preferably through an electromagnetic alternating field, more particularly preferably optically. The excitation preferably takes place in the light range from far infrared to far ultraviolet (in a range of from 100 nm to 30 μm wavelength), particularly preferably in the range of from near infrared to near ultraviolet (in a range of from 200 nm to 3 μm wavelength), more particularly preferably through visible light (in a range of from 400 nm to 800 nm wavelength). This can offer the advantage, with respect to the conventional global heating of the reaction vessel from externally, that the thermally insulating wall of the reaction vessel does not need to be overcome, as the energy is transferred directly to the nanoparticles. A quicker heating of the desired portion of the sample is thus achieved.

In a preferred embodiment of the invention the nanoparticles are excited by a laser. The laser light particularly preferably has a frequency that excites the surface plasmon resonance of the nanoparticles. The laser can provide the light pulsed or continuously. If the laser is pulsed, nanosecond lasers are preferably used. The laser can, e.g., be a gas laser, a diode laser or a diode-pumped solid body laser.

The duty factor is the ratio of the time interval of the excitation to the duration of a PCR cycle. The duty factor is preferably selected to be so great that the excitation leads to a sufficient denaturing of the DNA double strands through local heating. At the same time the duty factor is preferably selected so that the average temperature increase of the whole sample is kept sufficiently small so that no interfering influences on hybridization, elongation and denaturing arise. The duty factor for the irradiated volume is preferably less than 50%, particularly preferably less than 20% and more particularly preferably less than 1%. The duty factor in the irradiated volume is suitably more than $10^{-12}$, preferably more than $10^{-10}$, particularly preferably more than $10^{-9}$ and more particularly preferably more than $10^{-8}$.

In the sense of the present invention the power density is the optical power per unit area of the light impinging into the sample. If it is a pulsed light source the peak power is relevant. The power density, with which the nanoparticles are excited, is, preferably in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, more than 10 W/mm², particularly preferably more than 50 W/mm², particularly preferably more than 100 W/mm², particularly preferably more than 200 W/mm², particularly preferably more than 300 W/mm² and more particularly preferably more than 400 W/mm². With this embodiment of the invention it can be advantageously achieved that the nanoparticles are sufficiently heated through the excitation.

The power density, with which the nanoparticles are excited, is preferably less than 20,000 kW/mm², particularly preferably in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, less than 10,000 kW/mm², particularly preferably less than 5000 kW/mm², particularly preferably less than 3000 kW/mm², particularly preferably less than 1000 kW/mm², particularly preferably less than 500 kW/mm², particularly preferably less than 300 kW/mm², particularly preferably less than 150 kW/mm² and more particularly preferably less than 80 kW/mm². With this embodiment of the invention, damage to the nanoparticles or the DNA bound thereto can advantageously be counteracted or prevented. In a further preferred embodiment the energy of the light is transferred through the material absorption of the nanoparticles to these nanoparticles. The light used to excite the nanoparticles can also come e.g. from a thermal radiator, e.g. a flashing light. In a further preferred embodiment of the invention the nanoparticles are excited through an electromagnetic alternating field or electromagnetic waves that generate eddy currents in the nanoparticles. With a suitable form of the nanoparticles it is also possible to excite the nanoparticles with ultrasound.

In the sense of the present invention the duration of effect $t_A$ is the total duration, in which an energy source for the purpose of denaturing, e.g. during the passage of the cycle of the PCR, acts on a point in the sample with a power suitable for denaturing in order to bring about heating in the sample.

The energy source transfers during the whole time $t_A$ a power which is suited for denaturing to said point. An energy source in the form of a laser could be used for example with a higher power for denaturing and for a subsequent extinction measurement with lower power. In this case $t_A$ is merely the time, in which the laser transfers the higher power suitable for denaturing to the point.

If a plurality of energy sources are used for denaturing, $t_A$ preferably refers to the time, in which all energy sources for denaturing act simultaneously on the point. In the case of activation of a plurality of energy sources, frequently the denaturing will be achieved only with the simultaneous action.

Said point is thereby determined within the part of the sample, in which the method is carried out, so that $t_A$ assumes the greatest possible value. If therefore the heating is produced, for example, by a fixed Peltier element, $t_A$ is the total duration, in which heat flows from the Peltier element in this cycle to this point (typically approximately the switch-on duration during the heating step; in any case shorter than the cycle duration). If the heating is produced by a light beam with the diameter d, which is guided (scanned) with a speed v through the sample volume, $t_A$ is the time duration $$\frac{d}{v}$$

during which the light beam hereby acts on a point in the sample. If the heating is produced by a pulsed light source, of which the light beam is not moved relative to the sample during the pulse duration, the pulse duration is the duration of effect. If the heating is produced by a pulsed light source which is scanned through the sample, the shorter of the two durations (pulse duration and time duration $$\left.\frac{d}{v}\right)$$

is the duration of effect.

The duration of effect $t_A$, in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, is preferably more than 1 ps (picosecond), particularly preferably more than 30 ps, particularly preferably more than 100 ps, particularly preferably more than 300 ps, particularly preferably more than 1 ns (nanosecond), particularly preferably more than 10 ns, particularly preferably more than 100 ns, particularly preferably more than 300 ns, particularly preferably more than 1 μs (microsecond), particularly preferably more than 3 μs, particularly preferably more than 10 μs.

The duration of effect $t_A$, in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, is preferably less than 10 s (seconds), particularly preferably 1 s, particularly preferably less than 100 ms (milliseconds), particularly preferably less than 10 ms, particularly preferably less than 1 ms, particularly preferably less than 500 μs, particularly preferably less than 100 μs, particularly preferably less than 50 μs, particularly preferably less than 10 μs. The duration of effect $t_A$ is preferably shorter than it takes on average until the heat arising in the environment of the nanoparticles diffuses through the average particle distance, so that on average no significant overlap of the heat fronts of neighbouring particles takes place.

The duration of effect $t_A$ is, particularly preferably in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, selected so that the temperature increase around each irradiated nanoparticle on average at a distance of 20 nanoparticle diameters, particularly preferably 2 nanoparticle diameters, more particularly preferably 1 nanoparticle diameter, falls to less than half the temperature increase on the surface of the nanoparticles.

In one embodiment, a short irradiation duration per volume is preferred so that a de-hybridized DNA single strand can diffuse away from the nanoparticle, during the denaturing, only less than 100 nm (nanometres), particularly preferably less than 20 nm, particularly preferably less than 5 nm. There is thereby a high probability that the de-hybridized DNA single strand will bind to an oligonucleotide on the same nanoparticle ("re-hybridization"). This can facilitate an accelerated method according to the invention. For this, durations of effect $t_A$ of between 0.1 ns and 1000 ns are to be preferred, particularly between 1 ns and 300 ns.

In one preferred embodiment for the re-hybridization the concentration of the nanoparticles conjugated to primers is less than 10 nM. The duration of effect $t_A$ is preferably between 1 ns and 10 µs (microsecond), particularly preferably between 10 ns and 1 µs and more particularly preferably between 15 ns and 300 ns. The time interval of the excitation is preferably selected to be not substantially shorter than 1 ns, as otherwise the time of heating of the DNA double strand is not sufficient for the two contained single strands to be able to sufficiently separate from each other through diffusion so that they do not immediately hybridize with each other again.

The irradiation times per sample volume (i.e. the time during which a certain volume per cycle is optothermally irradiated for heating) are preferably below 1 s/µl, particularly preferably below 0.1 s/µl or 0.01 s/µl, or below 0.001 s/µl. The irradiation times per volume, as a function of the radiation source used, are preferably simultaneously greater than 1 ps/µl or preferably greater than 10 ps/µl or 100 ps/µl (e.g. when using pulsed laser), or in other embodiments (e.g. with lasers in CW operation) greater than 10 ns/µl, or 100 ns/µl.

The heating time, in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, is preferably less than 100 ms, particularly preferably less than 10 ms, particularly preferably less than 1 ms, particularly preferably less than 100 µs, particularly preferably less than 50 µs, particularly preferably less than 10 µs, particularly preferably less than 5 µs, particularly preferably less than 1.5 µs.

The heating time, in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, is preferably more than 1 ns, particularly preferably more than 5 ns, particularly preferably more than 10 ns.

The cooling time, in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, is preferably less than 100 ms, particularly preferably less than 10 ms, particularly preferably less than 1 ms, particularly preferably less than 100 µs, particularly preferably less than 50 µs, particularly preferably less than 10 µs, particularly preferably less than 5 µs, particularly preferably less than or 1.5 µs.

The cooling time, in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, is preferably more than 1 ns, particularly preferably more than 5 ns, particularly preferably more than 10 ns.

The heating time is the time that passes after the excitation intensity 1(t) of the light source has reached its maximum value in the respectively excited volume until a temperature is set at each point in the excited volume which changes, even if the duration of effect is doubled, by maximum 3° C.

The cooling time is the time duration after the switch-off point of the excitation light source that passes until at each point in the volume under observation a temperature is set that deviates by maximum 3° C. from the temperature before the effect.

The switch-off time point $t_{off}$ of the excitation light source is defined as the point in time at which the excitation intensity I in the volume under observation has decreased to less than 5% of the maximum excitation intensity (e.g. after the pulse of a laser).

Determination of the heating and cooling time: The evolution of the temperature over time at a distance r from the centre of a nanoparticle having radius rNP is obtained by numerically solving the heat conduction equation in a sufficiently large water sphere having radius rMax around the nanoparticle, wherein the nanoparticle itself is removed from the simulation area. By utilizing spherical symmetry, a one-dimensional radial heat conduction equation is obtained, in the area rNP to rMax, t>0:

$$\frac{\alpha}{r^2}\partial_r(r^2 \cdot \partial_r T(r, t)) = \partial_t T(r, t)$$

wherein T(r,t) is the temperature at the position r at the time t and $\alpha$ is the thermal diffusivity of the water ($\alpha=1,43\cdot 10^{-7}$ m²/s).

As a starting condition the temperature of the surrounding medium is set before optical excitation to $T_0$: $T(r, 0)=T_0$.

The boundary conditions at the positions rNP and rMax are set as follows: At the position r=rNP the increase of the temperature progression at the point in time t is obtained from the absorbed power of the nanoparticle at the point in time t (Neumann boundary condition): $\partial_r T(rNP, t)=P(t)/(4\cdot\pi\cdot rNP^2\cdot k)$, wherein P(t) is the power absorbed by the nanoparticle and k is the thermal conductivity of water (k=0.6 W/(m·K)). The absorbed power is calculated from F(t)=I(t)·σ, with I(t) corresponding to the time-dependent excitation intensity of the light source and the absorption cross-section of the particle σ. (i.e. provided that the focus size is not changed, I(t) for example for a CW laser would be a constant, and I(t) would reproduce the time-dependent pulse form for a pulsed laser).

At the position rMax the temperature is kept constant (T(rMax, t)=$T_0$.), Dirichlet boundary condition). For rNP<100 nm, for example rMax≥10,000 nm is selected. The thermal diffusivity and thermal conductivity of the water is assumed as a constant. In general $\alpha=k/(C\cdot\rho)$ applies, wherein C is the specific heat capacity and O the density of water.

By means of suitable programs for the numerical solution of such partial differential equations (e.g. with the command NSolve in mathematics, etc.) the above heat conduction equation can be solved and values obtained for the temperature as a function of the location and the time T(r,t).

For example, for a spherical gold nanoparticle with rNP=30 nm, which is excited with a constant intensity of 1 kW/mm² with 532 nm wavelength for a duration of 100 ns, the following values are obtained for a starting temperature of $T_0=30°$ C.: T(r=30 nm, t=20 ns)=70° C., T(r=30 nm, t=100 ns)=78° C., T(r=30 nm, t=120 ns)=36° C., T(r=40 nm, t=20 ns)=56° C., T(r=40 nm, t=100 ns)=64° C., T(r=40 nm, t=120 ns)=36° C.

To determine the heating time according to the invention T(r,t) is evaluated for different times. The heating time is then the shortest time $t_{auf}$, for which the following applies: with $|T(r, t_{auf})-T(r, 2·t_{auf})| \geq 3°$ C. with $r \in [rNP; rMAX]$; i.e. the amount of the difference of the temperature distribution for the times $t_{auf}$ and $2t_{auf}$ must be less than 3° C. for all points outside of the nanoparticle.

The cooling time is obtained as a difference $t_x-t_{off}$ wherein $t_x$ is the shortest time, for which the following applies: $|T(r, t_x)-T_0| \leq 3°$ C. with $r \in [rNP; rMAX]$ and $t_x > t_{off}$.

The concentration of the amplicon that is to be amplified in the method is, at the start of the method, preferably greater than $10^{-23}$ M (Mol/litre), particularly preferably greater than $10^{-21}$ M, particularly preferably greater than $10^{-20}$ M, particularly preferably greater than $10^{-19}$ M. It can advantageously be achieved through this embodiment of the invention that the amplification is sufficiently sensitive in order to produce an amount of amplification products that is suitable for detection.

The concentration of the amplicon that is to be amplified in the method is, at the start of the method, preferably less than 1 nM (Nanomol/litre), particularly preferably less than 30 pM (picomol/litre), particularly preferably less than 900 (Femtomol/litre), particularly preferably less than 800 fM (Femtomol/litre), particularly preferably less than 500 fM (Femtomol/litre), particularly preferably less than 100 fM, particularly preferably less than 30 fM. Through this embodiment of the invention it is advantageously possible to prevent the amplification already reaching saturation before its end.

The number of amplicons to be amplified in the method is, at the start of the method, preferably less than 500,000, particularly preferably less than 200,000, particularly preferably less than 100,000, particularly preferably less than 10,000. Through this embodiment of the invention it is advantageously possible to prevent the amplification already reaching saturation before its end.

In one embodiment of the invention the nucleic acids are amplified by means of a polymerase chain reaction (PCR), wherein a cycle consisting of the steps denaturing, annealing and elongation is repeatedly passed through.

The cycle can be passed through repeatedly until the desired degree of amplification is reached. The number of passages of the cycle of the polymerase chain reaction is preferably greater than 45, particularly preferably greater than 60, particularly preferably greater than 80, particularly preferably greater than 100, particularly preferably greater than 120, particularly preferably greater than 160, particularly preferably greater than 200. With a large number of passages of the cycle, a particularly high amplification can advantageously be achieved.

The number of passages of the cycle of the polymerase chain reaction is preferably less than 1000, particularly preferably less than 750, particularly preferably less than 500. With a number of passages of the cycle that is not too high, the duration of the amplification can be advantageously reduced. In addition, negative influences of impurities or the consumption or damage of reaction partners, such as for example a polymerase used in the method, can advantageously be kept low.

The PCR preferably uses nanoparticles conjugated to primers. When performing the PCR, preferably double-stranded PCR products are thereby produced, wherein in each case at least one single strand of the double-stranded PCR products is conjugated to a nanoparticle. Through excitation of the nanoparticles it can advantageously be achieved in this embodiment to produce the denaturing temperature around the nanoparticles and to perform the denaturing of the double-stranded PCR products without the whole reaction volume having to be heated. The denaturing can thereby be accelerated and the PCR thus takes place more quickly. In a further preferred embodiment, the annealing temperature and the elongation temperature are also produced through the excitation of the nanoparticles. In comparison with heating the whole sample to the annealing and elongation temperature, it is preferably only necessary to transfer a small amount of energy.

Denaturing, annealing and elongation of the PCR take place particularly preferably without global heating, but instead exclusively via local heating through excitation of the nanoparticles. In this way the method can be carried out without a means for global heating, so that less apparatus is required to carry out the method.

In a further preferred embodiment the method includes a global heating step. The temperature of at least one method step is reached at least partially through global heating. In a particularly preferred embodiment of the invention the method is a PCR and the annealing temperature is reached by global heating of the reaction volume. More particularly preferably, the reaction volume is maintained in a predetermined temperature range, in which the annealing takes place, throughout the whole method and beyond by global heating. The elongation temperature and the denaturing temperature are thereby reached through excitation of the nanoparticles. The means that generates the global heating can advantageously be kept very simple in its construction, as it must only maintain one predetermined temperature.

In a further preferred embodiment the annealing temperature and the elongation temperature are achieved by global heating and exclusively the denaturing is produced through excitation of the nanoparticles. It can advantageously be achieved that the means that brings about the global heating has to produce a temperature cycle with only two different temperatures and can thus be kept constructively simple. The elongation and the annealing usually take place in each case in a narrow temperature range. On the other hand, only one certain temperature must be surpassed for denaturing. Therefore, non-homogeneities in the excitation of the nanoparticles can be less of a problem for the production of the denaturing than when setting the annealing and elongation temperature. Consequently a preferred embodiment, in which the excitation of the nanoparticles serves exclusively for denaturing, can be realized technically more simply. In particular this applies to the particularly preferred case, in which the annealing temperature and the elongation temperature are very close to each other, e.g. with an annealing temperature of 60° C. and an elongation temperature of 72° C., so that global heating must only produce a small temperature increase.

In a particularly preferred embodiment the annealing temperature is equal to the elongation temperature. The method is hereby performed as a PCR. If the annealing temperature is equal to the elongation temperature, only one temperature cycle with two different temperatures is usually necessary to perform the PCR, whereby the method can be carried out in a simple structure. The melt temperatures of the primers and the DNA polymerase used are particularly preferably selected so that at the melt temperature the DNA polymerase used can still synthesize DNA at a sufficient speed. In a particularly preferred embodiment the elongation temperature, which is equal to the annealing temperature, is reached by global heating and the denaturing is achieved through excitation of the nanoparticles. In this way the means that brings about the global heating can have a simpler constructive design, as it only has to maintain one temperature.

In one preferred embodiment, the excitation of only a portion of the nanoparticles takes place at each point in time of the method. For this, e.g. the means serving for exciting the nanoparticles can be designed so that it excites the nanoparticles present only in a part of the reaction volume. In a particularly preferred embodiment the nanoparticles are optically excited by a laser, and the optics system that guides the light of the laser into the reaction volume is designed so that light is guided only into one part of the reaction volume. The portion of the nanoparticles that is excited preferably changes in the course of the method. In other words, a first amount of nanoparticles, which are excited at a first time point, is not identical to a second amount of nanoparticles, which are excited at a second time point. In this case any desired number of nanoparticles can be present in the first amount and any desired number of nanoparticles present in the second amount, provided that the first and second amounts are not identical. One of the two aforementioned amounts may, e.g., partially coincide with the other so that the two amounts form an intersection.

One of the amounts can, e.g., be a sub-amount of the other amount, so that one amount contains fewer nanoparticles than the other amount. The two amounts can e.g. also be designed so that they do not form an intersection and therefore no nanoparticle is simultaneously present both in the first amount and in the second amount. One of the two amounts can also be the empty amount (zero), so that e.g. nanoparticles are excited at one time point and no nanoparticles are excited at another time point. In a preferred embodiment the first and the second amounts contain substantially the same number of nanoparticles. A laser particularly preferably excites different portions of the nanoparticles at different times. In the embodiment of the method a laser can thereby be used with a lower power which just suffices to excite a portion of the nanoparticles. In a particularly preferred embodiment, two or more lasers are used to excite different portions of the nanoparticles. It is advantageously possible to excite different portions of the nanoparticles without an optical element being required that guides the laser onto different parts of the reaction volume.

In a further preferred embodiment of the invention a directed movement of the sample relative to an excitation field takes place so that nanoparticles in different sub-volumes of the sample are excited at different times. The excitation field is particularly preferably the light of a laser. In a more particularly preferred embodiment the light of the laser is guided by an optical element so that nanoparticles in different sub-volumes of the reaction volume are excited with the light at different times. The optical element can be arranged to be movable, e.g. the optical element can contain a movable mirror, a spatial modulator or an acousto-optic modulator. The laser itself can also be arranged to be movable. The movement of the sample can also be realized so that the reaction vessel containing the sample is moved. In a particularly preferred embodiment both the laser beam and also the reaction vessel are moved. In a further preferred embodiment the sample is moved in the reaction volume, so that the light of the laser detects different sub-volumes of the sample at different times. This can be achieved e.g. by the sample being mixed in the reaction volume, e.g. by a magnetic agitator. The reaction volume can e.g. be in an elongated form, e.g. a duct or a tube. The sample can e.g. be moved through a duct, wherein the sample passes through a laser beam at one or more positions. A sample particularly preferably flows through a duct and passes n positions, at each of which a laser beam is directed onto the sample in the duct, wherein through the linear flow of the sample through the n laser beams a PCR with n cycles is carried out. The method can be advantageously carried out with a small number of movable parts. By using a duct, a miniaturisation, e.g. in the sense of a lab-on-chip, is also possible. The denaturing is preferably produced through the laser beam, while the elongation and annealing temperature are produced by global heating. The elongation temperature is particularly preferably equal to the annealing temperature so that only one temperature has to be maintained by global heating. In this way the method according to the invention can advantageously be carried out with a low level of resources.

In a preferred embodiment a DNA polymerase that is thermolabile is used in the method. If the excitation of the nanoparticles is used for denaturing it is possible to avoid the whole reaction volume being exposed to high temperatures. It is instead possible to bring only the direct environment of the nanoparticles to the denaturing temperature. The DNA polymerases that are not located in this direct environment are not therefore exposed to high temperatures. It is thereby possible to also use DNA polymerases that are not heat-stable, thus thermolabile. Through the inclusion of the thermolabile DNA polymerases, therefore, a larger selection of DNA polymerases is available for the method according to the invention. Through the greater selection of DNA polymerases the reaction conditions can be changed to a greater extent and at the same time a sufficient functioning of the respective DNA polymerase can be maintained. In order that the nucleic acids to be amplified can bind to the negatively charged oligonucleotides on the nanoparticles, it may be necessary to use substances—in particular salts—in the sample in a concentration that negatively influence the functioning of a thermostable DNA polymerase, which reduces the efficiency of the method. The greater selection of DNA polymerases—in particular those having a high tolerance for salts—can lead to an increase in the efficiency of the method being achieved. Part of the larger selection of DNA polymerases are small DNA polymerases such as e.g. the Klenow fragment and Phi29. In the proximity of the nanoparticles, large thermostable DNA polymerases can experience a steric hindrance through the applied and possibly already elongated primers. It can thereby arise that the DNA polymerase does not arrive at the nucleic acid to be copied or the DNA polymerase breaks off before it has synthesized a complete copy of the original or complement, which signifies a reduction in the efficiency of the method. The greater selection of DNA polymerases thus facilitates an increase in the efficiency of the method. Through the larger selection of DNA polymerases, enzymes with lower production costs are also advantageously available. The DNA polymerases that are not located in the direct proximity of the nanoparticles experience a lower heat-related deactivation. It is thereby advantageously possible to use a smaller amount of DNA polymerase in the method.

In a preferred embodiment of the invention, both soluble primers and also primers on nanoparticles are present in the reaction volume. The soluble primers are not conjugated to nanoparticles, but instead are dissolved in the sample. The soluble primers have preferably smaller dimensions than the nanoparticle-primer conjugates and can be present in a higher concentration than the nanoparticle-primer conjugates. Therefore, the soluble primers can have better and quicker access to long, double-stranded nucleic acids such as e.g. genomic DNA. In a particularly preferred embodiment, in a first step of the method the long, double-stranded nucleic acids are denatured by global heating of the whole reaction volume, after which the dissolved primers hybridize with the nucleic acids. The PCR thereby initially takes place in one or more cycles with global heating, the DNA polymerase thereby synthesizes the desired, short copies of the long, double-stranded nucleic acids. After this, the PCR is continued, wherein local heating is also used through excitation of the nanoparticles.

DETAILED DESCRIPTION OF THE INVENTION BY REFERENCE TO A PLURALITY OF EXEMPLARY EMBODIMENTS

FIG. 1A-FIG. 1H show in a schematic illustration the nanoparticles according to the invention which are conjugated to filling molecules, spacer sequences, abasic modifications and primer sequences.

Figure 1A:
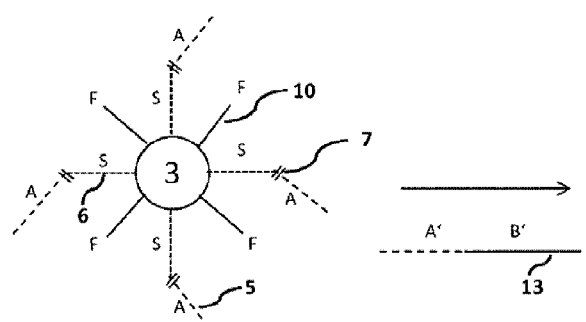
FIG. 1A shows in a schematic illustration the primer sequences, spacer sequences, abasic modification and filling molecules, and which also has dNTPs and DNA polymerase.

FIG. 1A-FIG. 1H show an exemplary embodiment of the method according to the invention for the amplification of nucleic acids 1, which is carried out as a PCR. First nanoparticles 3 are contained in a reaction volume 2. The first nanoparticles 3 have oligonucleotides 4 at their surface, as shown in FIG. 1A. One class of oligonucleotides 4 contains, in each case as a sub-sequence, a primer sequence 5 with the sequence A and, as a further, optional sub-sequence, a spacer sequence 6 S and an optional abasic modification 7 between the primer sequence 5 A and spacer sequence 6 S. The spacer sequence 6 S is used to keep the primer sequence 5 far enough away from the surface of the nanoparticles 9 so that a nucleic acid 1 to be amplified can bind with better efficiency to the primer sequence 5 and the DNA polymerase 11 can find better access to the primer sequence 5. The abasic modification 7 prevents the spacer sequence being overwritten by the polymerase 11. The oligonucleotides 4 with the primer sequence 5 A are, e.g., fixed with a thiol bonding at the surface of the first nanoparticles 3, so that the 3' end faces away from the first nanoparticle 3. Optionally, a further class of oligonucleotides 4 can be located on the surface of the first nanoparticles 3, these are the filling molecules 10 F. With the filling molecules 10 the charge of the nanoparticles 9 can be modulated so that undesired aggregations of the nanoparticles 9 do not arise. In addition the filling molecules 10 can increase the distance of the primer sequences 5 to each other on the surface of the nanoparticles 9, so that the nucleic acids 1 to be amplified and the DNA polymerase 11 have better access to the primer sequences 5. This can increase the efficiency of the method. The spacer sequence 6 is thereby preferably at least as long as the filling molecules 10, so that the primer sequences 5 advantageously project out of the filling molecules 10.

Figure 1B:
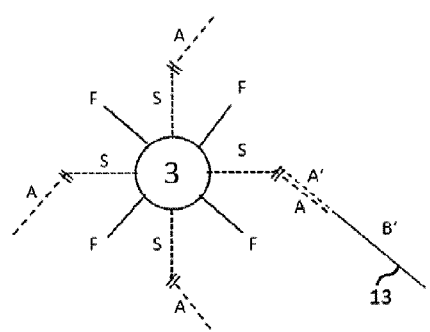
FIG. 1B shows in a schematic illustration the original with its subsequence A' binding to the primer sequence on the surface of the first nanoparticles.
Figure 1D:
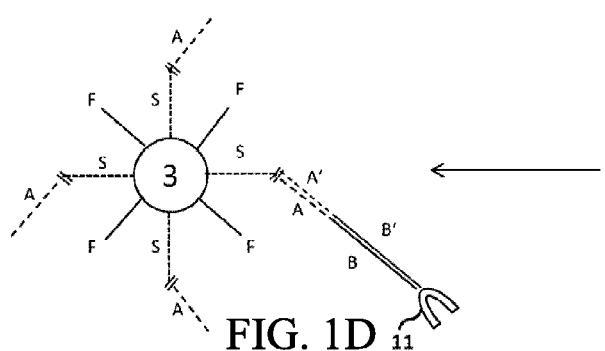
FIG. 1D shows in a schematic illustration of an elongation step based on the end of the primer sequence, a nucleic acid that is complementary to the original, is referred to as a complement and is combined with the spacer sequence on the surface of the first nanoparticle.
Figure 1C:
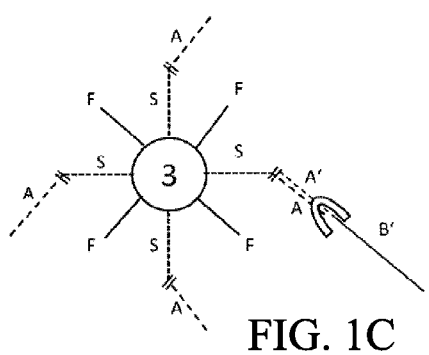
FIG. 1C shows in a schematic illustration that a DNA polymerase binds to the original and the primer sequence hybridized with the original.
Figure 1E:
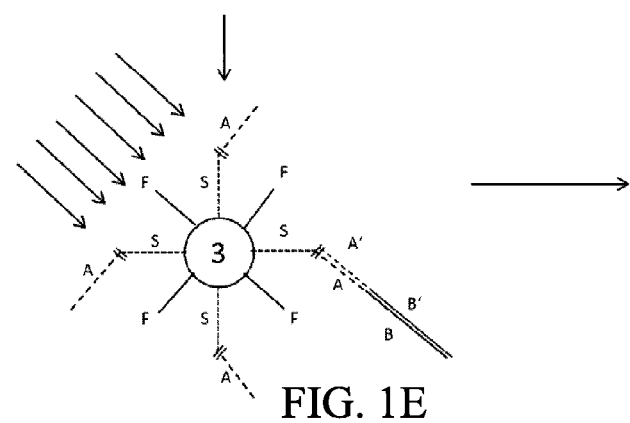
FIG. 1E shows in a schematic illustration where the first nanoparticle is then irradiated with light, which is absorbed by the first nanoparticle due to its plasmonic or material properties and is converted into heat.
Figure 1F:
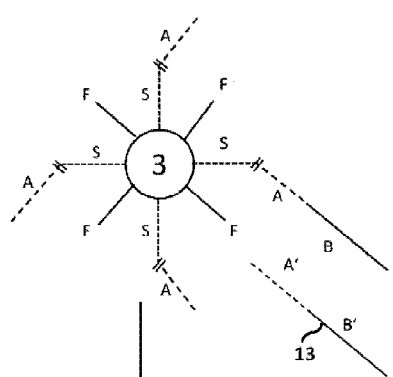
FIG. 1F shows in a schematic illustration where the original is now free again, so that it can bind to a further primer sequence and further nanoparticle-bound complements can be synthesized in further cycles of the method.

In the reaction volume 2 there is a sample 12, which contains the first nanoparticles 3 of FIG. 1A with the primer sequences 5, spacer sequences 6, abasic modification 7 and filling molecules 10, and which also has dNTPs and DNA polymerase 11, in addition, further reagents necessary for a PCR. A nucleic acid 1 to be detected can be present in the sample 12. In this exemplary embodiment the nucleic acid 1 to be detected is a DNA single strand, which is also described as the original 13, and has a sub-sequence A' and also a sub-sequence B'. The original 13 can also have further sub-sequences, e.g. as overhangs at the 5' or 3' end or between the two sub-sequences A' and B'. In FIG. 1B, the original 13 with its sub-sequence A' binds to the primer sequence 5 A on the surface of the first nanoparticles 3. In FIG. 1C, it is shown that a DNA polymerase 11 binds to the original 13 and the primer sequence 5 A hybridized with the original 13. Then, the DNA polymerase 11 synthesizes, in an elongation step shown in FIG. 1D, based on the 3' end of the primer sequence 5 A, a nucleic acid 1 that is complementary to the original 13 and is referred to as a complement 14 and is combined with the spacer sequence 6 on the surface of the first nanoparticle 3. In FIG. 1E, the first nanoparticle 3 is then irradiated with light, which is absorbed by the first nanoparticle 3 due to its plasmonic or material properties and is converted into heat. The heat is emitted to the environment of the first nanoparticle 3 and is sufficient in the area of the original 13 and the newly synthesized complement 14 hybridized with it so that the original 13 can denature from the complement 14. The original 13 is now free again, as shown in FIG. 1F, so that it can bind to a further primer sequence 5 and further nanoparticle-bound complements 14 can be synthesized in further cycles of the method. This produces a linear increase in the concentration of the complements 14 with an increasing number of cycles.

Figure 1H:
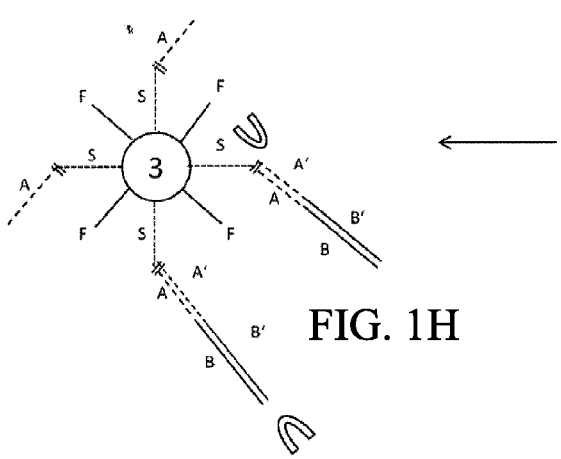
FIG. 1H shows in a schematic illustration the original, the copy of the original and the two complements combined with the first nano particle.
Figure 1G:
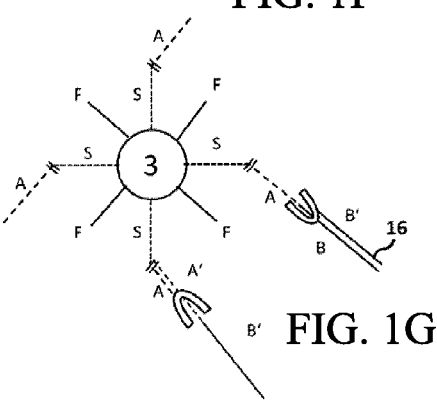
FIG. 1G shows in a schematic illustration that the already synthesized complement with the sub-sequences A and B, which is combined via a spacer sequence and an abasic modification on the surface of the first nanoparticle, is hybridized with a primer that was previously free in the sample.

In one embodiment of the method, after the extension of the primer sequence 5 on the surface of the first nanoparticles 3, wherein a nanoparticle-bound complement 14 is produced, a free reverse primer 16 is used which binds to the 3' end of the complement. It is shown in FIG. 1G that the already synthesized complement 14 with the sub-sequences A and B, which is combined via a spacer sequence 6 and an abasic modification 7 on the surface of the first nanoparticle 3, is hybridized with a primer 8 B' that was previously free in the sample 12. The primer 8 has the sequence B' and is combined with the sub-sequence B of the complement 14. Starting from the primer 8 with the sequence B', the DNA polymerase synthesizes a copy of the original 13. It is also shown in FIG. 1G that the original 13 has bonded to a further primer sequence 5 A on the surface of the first nanoparticle 3 and a DNA polymerase 11 starting from the primer sequence 5 A synthesizes a further complement 14. The original 13, the copy of the original 13 and the two complements 14 combined with the first nanoparticle are shown in FIG. 1H. A subsequent denaturing through excitation of the first nanoparticles 3 leads to the original 13 and its copy becoming free. Both the original 13 and also its copy can thereby serve in subsequent steps of the method as a template for amplification. After a waiting period, which is possibly necessary for the hybridization of the original 13 and copies of the original 13 with primer sequences 5 A on the first nanoparticles 3, and free primers 8 B' with primer sequences 5 already elongated on the first nanoparticles 3, the next cycle of the method can be carried out with a further excitation of the first nanoparticles 3. The cycle is preferably repeated until a sufficient number of extended primer sequences 5 are located on the first nanoparticles 3 and/or a sufficient number of copies of the original 13 are located in the sample 12, in order to be able to carry out a detection of the completed amplification or the presence of the original 13 in the sample 12. Through a free primer 8 B', as shown in FIGS. 1G and 1H, an exponential amplification of the original 13 is possible. In FIGS. 1A to 1F, without this free primer 8, however, only a linear amplification of the nanoparticle-bound complement 14 can be achieved.

FIG. 2A-FIG. 2E shows in a further schematic illustration the nanoparticles according to the invention which are conjugated to filling molecules, spacer sequences, abasic modifications and primer sequences.

Figure 2A:
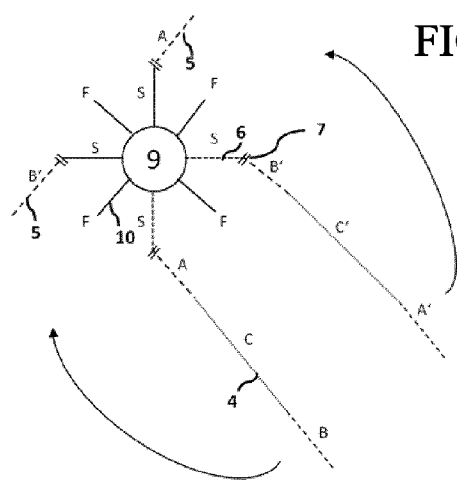
FIG. 2A shows in a further schematic illustration where a DNA single strand with the sequence is now located on the nanoparticle. The copy of the original fixed on the nanoparticle, with its subsequence, hybridizes to a primer sequence on the surface of the same nanoparticle. A complement synthesized on the surface of the nanoparticle, with its sub-sequence A', hybridizes to a primer sequence on the surface of the same nanoparticle.
Figure 2B:
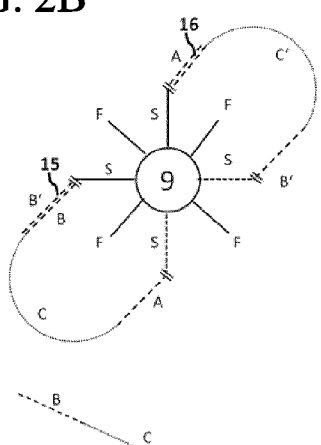
FIG. 2B shows in a further schematic illustration the result of the two aforementioned hybridizations.
Figure 2C:
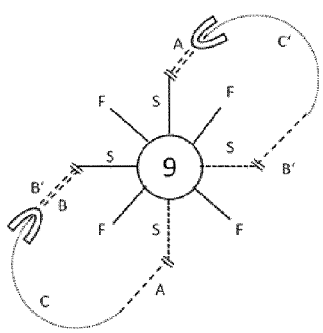
FIG. 2C shows in a further schematic illustration that, starting from the primer, a strand complementary to the original is synthesized, which is combined via a spacer sequence with the surface of the nanoparticle. Through a further DNA polymerase, starting from the primer sequence, a copy of the original is synthesized, which is also combined via a spacer sequence with the surface of the nano particle.
Figure 2D:
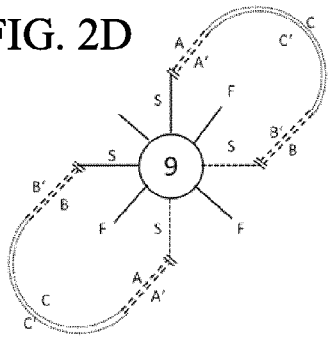
FIG. 2D shows in a further schematic illustration the result of the two above syntheses.
Figure 2E:
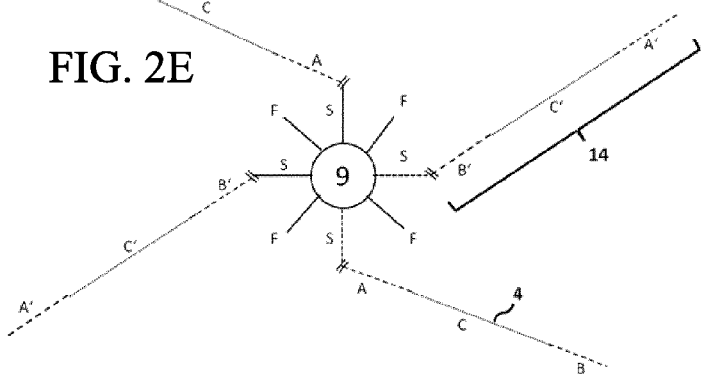
FIG. 2E shows a further schematic illustration of a complement which is fixed on the surface of another, identical nanoparticle.

FIG. 2A-FIG. 2E show an embodiment of the method according to the invention, in which nanoparticles 9 are located in a sample 12. The nanoparticles 9 have filling molecules 10 F at their surface. Furthermore the nanoparticles 9 are conjugated to oligonucleotides 4. A first class of oligonucleotides 4 consist of a spacer sequence 6 S and a primer sequence 5 A and an optional abasic modification 7 between the primer sequence 5 A and spacer sequence 6 S. A second class of oligonucleotides 4 consist of a spacer sequence 6 S and a primer sequence 5 B' and an optional abasic modification 7 between the primer sequence 5 B' and spacer sequence 6 S. The original 13 to be amplified is a single-stranded DNA molecule with the sub-sequences A, C and B (not shown) in this exemplary embodiment. Through a DNA polymerase 11, a strand complementary to the original 13, starting from the primer sequence B' has been synthesized on the surface of the nanoparticle 9 so that, as shown in FIG. 2A, a DNA single strand with the sequence S, B', C' and A' is now located on the nanoparticle 9. At the same time it can be seen in FIG. 2A that through a DNA polymerase a copy of the original 13 starting from the primer sequence 5 A, which is combined with the spacer sequence 6 S and the optional abasic modification 7 on the surface of the nanoparticle 9, has been synthesized. As shown by an arrow in FIG. 2A, the copy of the original 13 fixed on the nanoparticle 9, with its sub-sequence B, hybridizes to a primer sequence 5 B' on the surface of the same nanoparticle 9. A second arrow in FIG. 2A shows that the complement 14 synthesized on the surface of the nanoparticle 9, with its sub-sequence A', hybridizes to a primer sequence 5 A on the surface of the same nanoparticle 9. The result of the two aforementioned hybridizations is shown in FIG. 2B. Both the original 13 and also the complement 14 form a loop on the surface of the nanoparticle 9. It can be seen in FIG. 2C that, starting from the primer 8 B', a strand complementary to the original 13 is synthesized, which is combined via a spacer sequence 6 S with the surface of the nanoparticle 9. Through a further DNA polymerase 11, starting from the primer sequence 5 A a copy of the original 13 is synthesized, which is also combined via a spacer sequence 6 with the surface of the nanoparticle 9. The synthesis of the polymerase 11 ends respectively at the abasic modification 7. The result of the two syntheses can be seen in FIG. 2D. In this embodiment, both the forward primer 15 and also the reverse primer 16 are located on the same nanoparticle 9. In this way, a newly synthesized DNA strand can hybridize back to a primer 8 on the same nanoparticle 9. This can lead to an acceleration of the method according to the invention, as the newly synthesized DNA strand does not have to cover a long distance in order to meet a complementary primer 8. Instead, the newly synthesized DNA strand can bind particularly rapidly to a complementary primer 8 on the surface of the same nanoparticle 9, which is particularly facilitated by the local concentration of the primers 8 on the nanoparticle 9 being particularly high. After the excitation of the nanoparticle 9 in FIG. 2D, for example by a laser 17, the copies of the original 13 and the copies of the complement 14, which are each fixed via spacer sequences 6/optional abasic modifications 7 on the surface of the nanoparticle 9, de-hybridize. Then a copy of the original 13, which is fixed to a nanoparticle 9, can hybridize with a complement 14 which is fixed on the surface of another, identical nanoparticle 9. Through the hybridization the nanoparticles 9 are combined, so that a measurable change arises. The measureable change can be for example a colour covering of the sample 12. It is possible through the embodiment of the method according to the invention shown in FIGS. 2A to 2E to provide a simple test to serve for the detection of the original 13.

Figure 3:
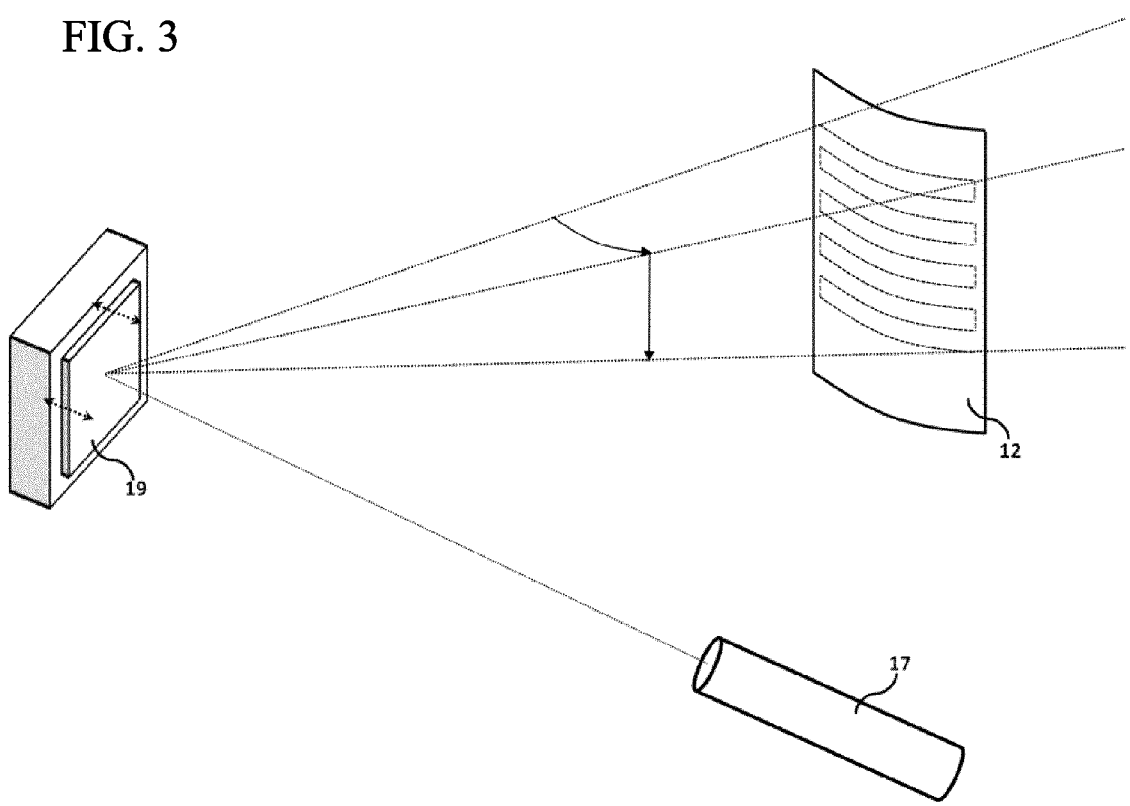
FIG. 3 shows in a schematic illustration a structure for carrying out the method according to the invention with a laser, a two-dimensional mirror scanner and a sample.

FIG. 3 shows a structure that is suited for carrying out the method according to the invention. The structure contains a light source 18, which is implemented in this example as a laser 17, and a two-dimensional mirror scanner 19, which can guide light from the laser 17 to the sample 12. The two-dimensional mirror scanner 19 can thereby deflect the laser beam in two dimensions. The denaturing in the sample 12 takes place in this structure in that a laser beam is focused on a part of the sample 12. In the course of the method the laser beam is deflected so that it impinges on different parts of the sample 12. In the example shown in FIG. 3, the laser beam is deflected by the mirror scanner 19 in such a way that the laser beam travels linearly over the reaction volume 2, in which the sample 12 is located. The path covered by the laser beam is shown in broken lines in FIG. 3 in the sample 12. Due to the fact that at each time point of the method only parts of the sample 12 are excited, laser 17 with a lower power can be used. As excitations of less than a microsecond suffice in order to denature DNA with the aid of optothermally heated nanoparticles 9, with typical focus diameters of a laser 17 of approximately 10 to 100 µm, a laser beam with a speed of approximately 10 to 100 m/s can scan the sample 12 and thereby lead to a denaturing of the DNA at each point over which the laser beam travels. This facilitates a very rapid scanning also of large sample volumes. The complete scanning of a surface area of 1 cm$^2$ lasts only 128 ms, e.g. with a focus diameter of 78 µm and 128 lines at a line distance of 78 µm and a line length of 1 cm, at a speed of the scanning laser beam of 10 m/s. If the volume has e.g. a depth of 10 mm, a volume of 1 ml can be processed (for this it must of course be ensured, inter alia, that the intensity of the excitation is sufficiently high over the whole depth). This is advantageously substantially shorter than would generally be required by a denaturing step by global heating. With optical elements such as e.g. a mirror scanner 19 shown in FIG. 3, which can be designed as a galvanometric scanner, and so-called F theta lenses, a good homogeneity of the focus quality and size can be achieved over the whole scanned sample 12. Alternatively to a continuously emitting laser 17, a pulsed laser 17 or a thermal radiator can also be used.

Figure 4:
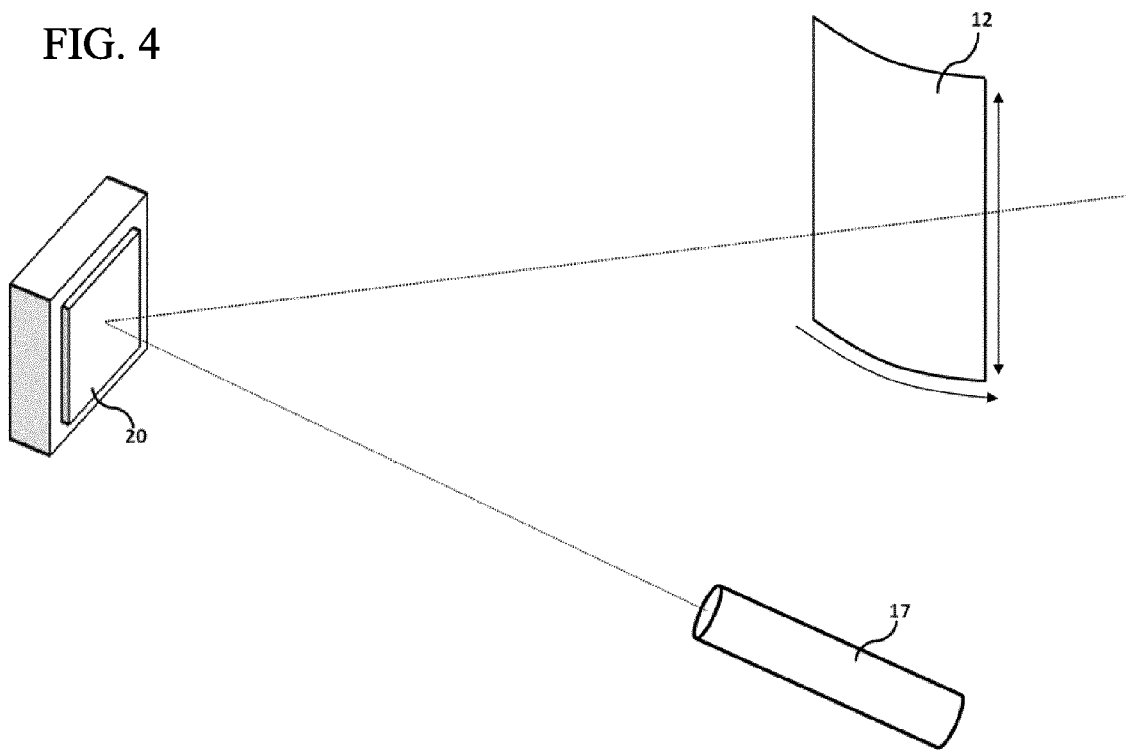
FIG. 4 shows in a schematic illustration a further structure for carrying out the method according to the invention with a laser, a mirror and a sample moved relative to the laser beam.

FIG. 4 shows a structure for carrying out the method according to the invention, wherein there is a laser 17 and a mirror 20 is arranged immovably, and the laser beam of the laser 17 is guided by the mirror 20 onto the sample 12. The sample 12 is arranged to be movable in two dimensions so that, by moving the sample 12, the whole sample 12 or large parts of the sample 12 can be detected by the focus of the laser 17.

Figure 5:
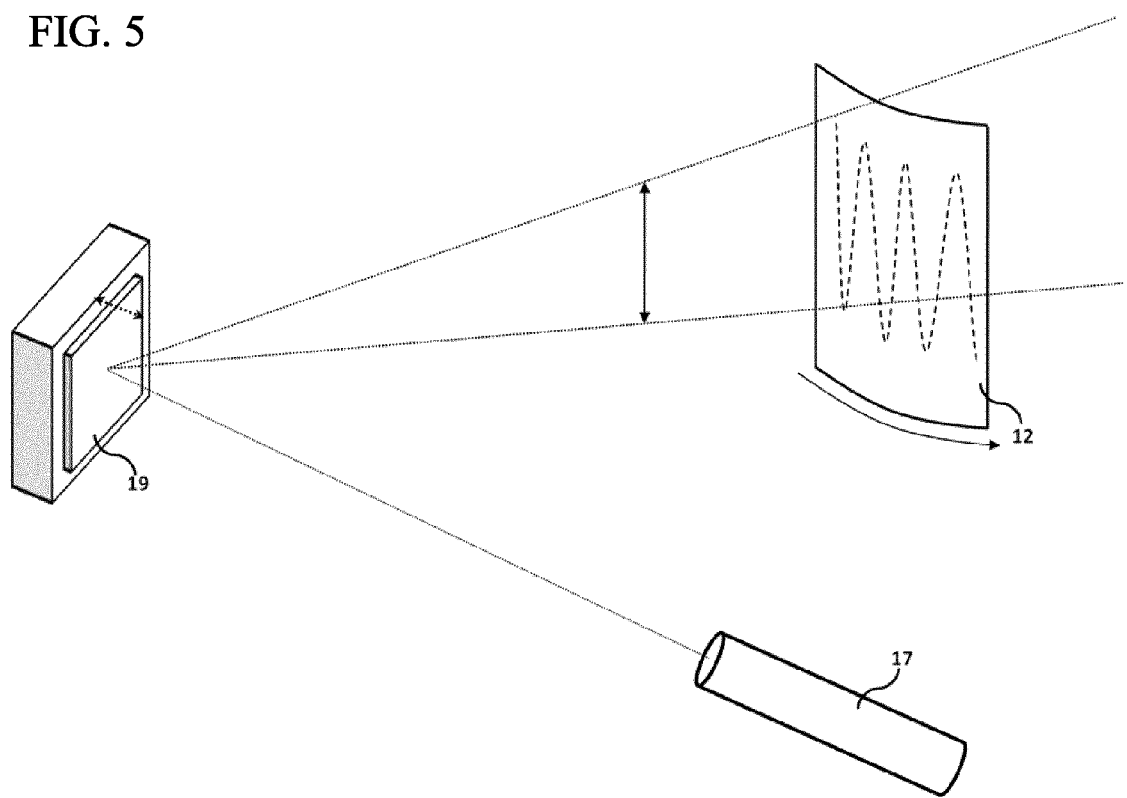
FIG. 5 shows in a schematic illustration a further structure for carrying out the method according to the invention with a laser, a one-dimensional mirror scanner and a one-dimensionally moved sample.

FIG. 5 shows a structure for carrying out the method according to the invention, wherein a laser 17 is arranged to be immovable and a mirror scanner 19 can deflect the laser beam of the laser 17 in one direction. The sample 12 is arranged to be movable in one direction, so that, by moving the mirror scanner 19 and the sample 12, the whole sample 12 or large parts of the sample 12 can be detected by the laser beam.

FIG. 6A-FIG. 6F shows in a schematic illustration the nanoparticles according to the invention and the test probes according to the invention for positive detection of DNA.

Figure 6A:
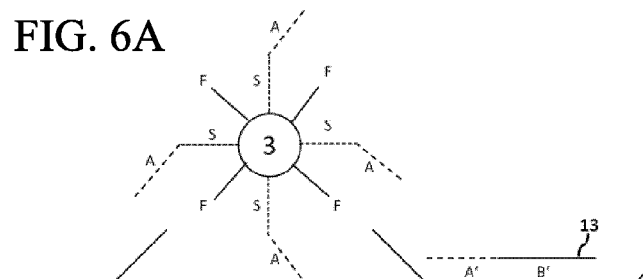
FIG. 6A shows in a schematic illustration the first oligonucleotides which consist of a spacer sequence and a primer sequence.
Figure 6B:
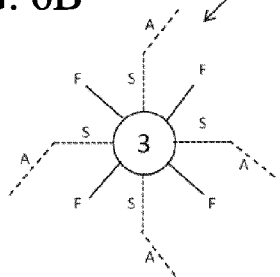
FIG. 6B shows in a schematic illustration where, if the original is not present in the sample, no complement is produced at the surface of the first nanoparticles.
Figure 6C:
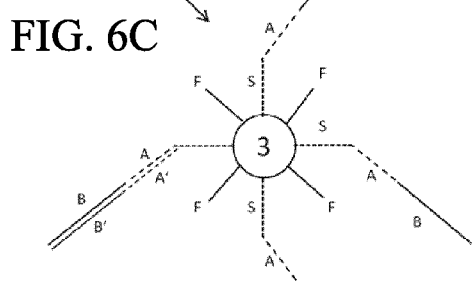
FIG. 6C shows in a schematic illustration that the complement is combined via the spacer sequence with the surface of the first nano particle.
Figure 6D:
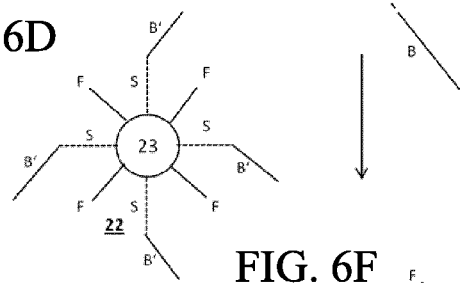
FIG. 6D shows in a schematic illustration the test probes which are provided to the sample.
Figure 6E:
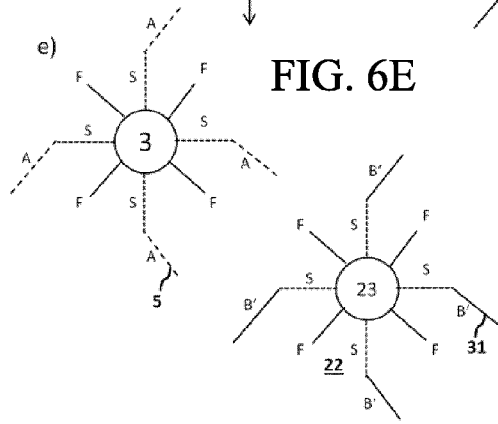
FIG. 6E shows in a schematic illustration where there is no complement on the first nanoparticles, first nanoparticles and second nanoparticles cannot combine, and the measurable change does not arise.
Figure 6F:
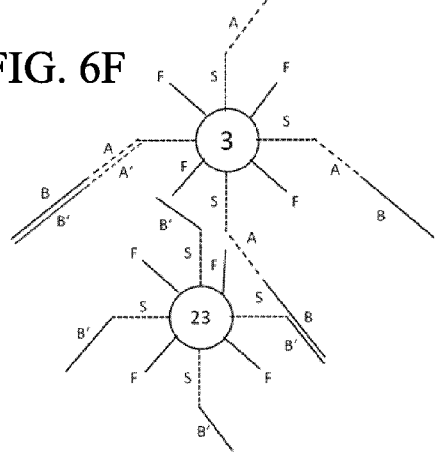
FIG. 6F shows in a schematic illustration that the test sequence can hybridize with the complementary sub-sequence of the complement on the surface of the first nanoparticle.

One possibility for the detection of a nucleic acid 1 through PCR according to the invention is shown in FIG. 6A-FIG. 6F. First nanoparticles 3, which have filling molecules 10 F and first oligonucleotides 21 at their surface, are located in a sample. The first oligonucleotides 21 consist of a spacer sequence 6 S and a primer sequence 5 A, as shown in FIG. 6A. If an original 13 with the sub-sequences A' and B' is present in the sample 12, the original 13 hybridizes onto the complementary primer sequence 5 A on one of the first nanoparticles 3. Through a DNA polymerase 11, starting from the primer sequence 5 A, the complement 14 with the sub-sequences A and B is written, so that the complement 14 is combined via the spacer sequence 6 S with the surface of the first nanoparticle 3, as shown in FIG. 6C. In a next step, the test probes 22 shown in FIG. 6D are provided to the sample. The test probes 22 are second nanoparticles 23, which have filling molecules 10 and second oligonucleotides at their surface. The second oligonucleotides contain a spacer sequence 6 S and a test sequence 5 B'. The test sequence 5 B' can hybridize with the complementary subsequence B of the complement 14 on the surface of the first nanoparticle 13, as shown in FIG. 6F. First nanoparticles 3 and second nanoparticles 23 are thereby combined so that a measurable change can arise. If the original 13 is not present in the sample 12, no complement 14 is produced at the surface of the first nanoparticles 3, as can be seen in FIG. 6B. Since, however, there is no complement 14 on the first nanoparticles 3, first nanoparticles 3 and second nanoparticles 23 cannot combine and the measurable change does not arise. The sequence B' in this embodiment is complementary to the sequence B, but can also be complementary to parts of the sequence A. The spacer sequence 6 S on the first nanoparticles 3 is identical to the spacer sequence 6 S on the second nanoparticles 23. In a further embodiment, however, different spacer sequences 6 can also be used on the first nanoparticles 3 and second nanoparticles 23. Several different spacer sequences 6 can also be used on the same class of nanoparticles. The buffer and hybridization conditions, e.g. temperature, salt concentrations, nanoparticle concentrations, concentrations of other buffer additives, pH value, are preferably selected so that hybridization can arise only after completed extension of the primer sequence 5 A on the first nanoparticles 3, this hybridization combining the first nanoparticles 3 with the second nanoparticles 23. The combination of the first nanoparticles 3 with the second nanoparticles 23 can, e.g., be detected as redshift and broadening of the plasmon resonance in the extinction spectrum. The combination can also, e.g., be detected by measuring the transmission change in one or more wavelengths after optothermal excitation of the nanoparticles and resulting denaturing of the nucleic acids 1, which combine the first nanoparticles 3 with the second nanoparticles 23. The test probes 22 can be made available in a special hybridization buffer, to which at least a part of the sample 12, which contains the first nanoparticles 3, is added, after the method step that allows the synthesis of the complement 14. The test probes 22 can also be present already before the start of the method in the sample together with the first nanoparticles 3. In this case the test probes 22 can be passivated so that they do not act as primers 8. The passivation of the test probes 22 can involve the primer sequence 5 on the test probes 22 being selected so that, at the annealing temperature during the PCR, no hybridization of the said primer sequence 5 with the original 13 takes place, but instead only after subsequent reduction of the temperature. The passivation of the test probes 22 can also take place by the second oligonucleotides, which contain sub-sequences of the original 13, being fixed at the 3' end on the second nanoparticles 23, so that the DNA polymerase 11 cannot extend the second oligonucleotides. In this case the second oligonucleotides can be free at their 5' end or combined with the second nanoparticles 23. The test probes 22 can also be passivated by a base modification, e.g. with dideoxy cytosine (ddC), at the 3' end of the second oligonucleotides preventing the extension.

In the embodiment of the method shown in FIG. 6A-FIG. 6F, first nanoparticles 3 of gold with a diameter of 60 nm are functionalized with oligonucleotides 4 (according to J. Hurst et al., Anal. Chem., 78(24), 8313-8318, 2006, the related content of which is part of the present disclosure by virtue of reference thereto). For one part, oligonucleotide 4 ID1 is used and, as a filling molecule 10, for four parts, oligonucleotide 4 ID2 is used. After functionalization and 6 washing steps, the first nanoparticles 3 are present in a concentration of 200 pM in a PBS buffer (20 mM PBS, 10 mM NaCl, 0.01% Tween 20, 0.01% acid, 1 mM EDTA, pH 7.5). The amplification reaction is carried out in a total volume of 10 μl in 200 μl sample tubes 24 (5 μl DreamTaq PCR Mastermix 2x (obtained from Fermentas), 0.1 μl NaCl 5 M, 0.1 μl $MgCl_2$ 250 mM, 0.1 μl $MgSO^4$ 250 mM, 1 μl of the functionalized first nanoparticles 200 pM, 1 μl oligonucleotide 4 ID3 (as original 13 to be amplified, the concentration of the original 13 to be determined thereby contributes in the total volume of 10 μl, e.g. 0 pM, 10 pM, 20 pM or 50 pM) dissolved in water with 100 nM oligonucleotide 4 ID4 (oligonucleotide 4 ID4 hereby serves for saturation of surfaces, e.g. during the storage of the original 13 before the reaction), 2.7 μl water).

Figure 7:
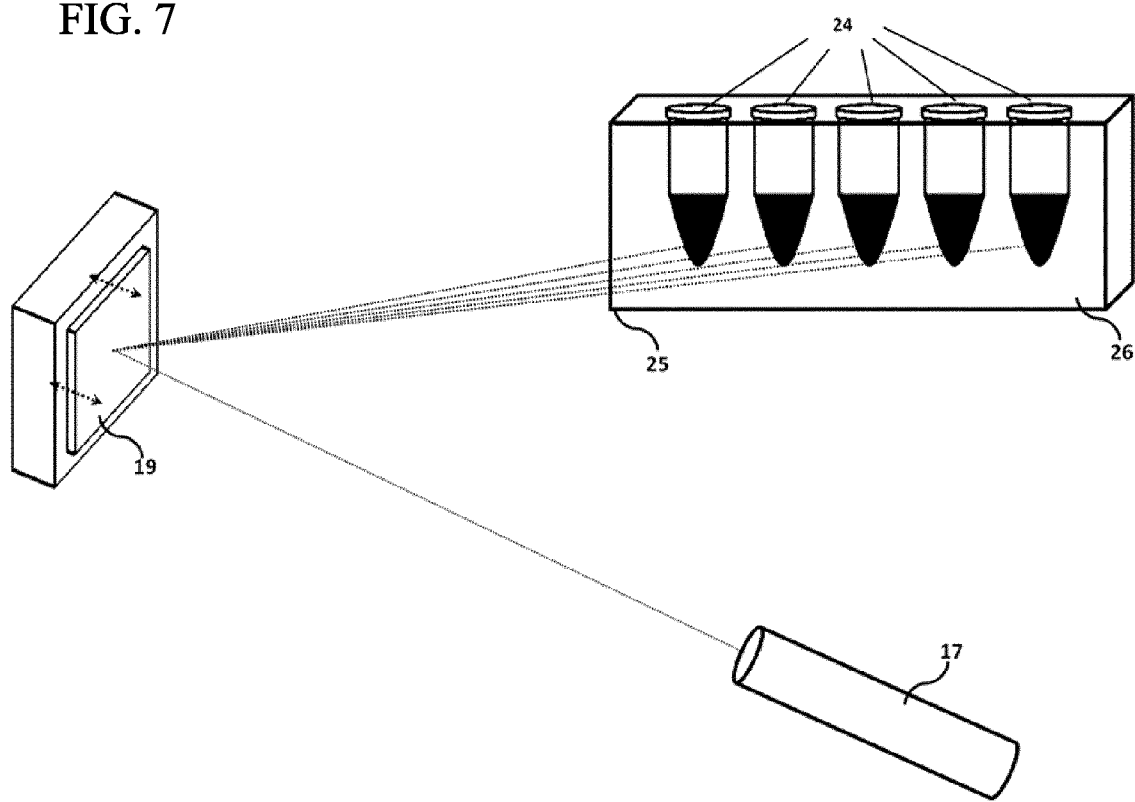
FIG. 7 shows in a schematic illustration a further structure for carrying out the method according to the invention with a laser, a two-dimensional mirror scanner and sample tubes in a water bath.
Figure 12:
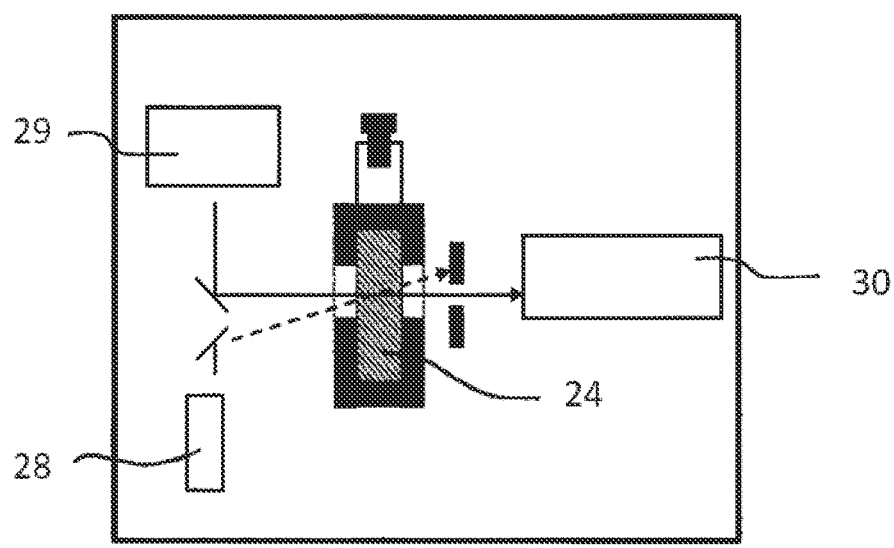
FIG. 12 shows in a schematic illustration a first laser for excitation of nanoparticles in a sample tube and a second laser and a photodiode for measuring the transmission of the sample.

As shown in FIG. 7, the sample tubes 24 are brought in a glass cuvette 25 in a water bath 26 to a temperature of 65° C., which constitutes both the annealing temperature and the elongation temperature. The water bath 26 serves, besides tempering, also for improved introduction of the laser 17 into the non-planar surface of the sample tubes 24. The water in the water bath 26 allows the refractive index difference between the outside and the inside of the sample tubes 24, filled with PCR reaction mix, to be reduced and to therefore prevent a refraction of the laser beam and hence a negative influence on the focus quality and sharpness. The coupling of the laser 17 is thereby advantageously improved. The laser 17 which is used to excite the nanoparticles is a frequency-doubled diode-pumped Nd:YAg-Laser (Coherent Verdi V10), which is focused, with an output power of 1.5 W with a F-Theta lens (Jenoptik, focal length 100 mm) behind a mirror scanner 19 (Cambridge Technologies, Pro Series 1) into the sample tubes 24 in the water bath 26 (focus diameter approximately 20 μm). The mirror scanner 19 allows the focus to move line by line through the sample tubes 24, as also already shown in FIG. 3, and thus allows the whole PCR reaction volume to participate in the optothermal amplification. For each sample tube 24, 400 lines with a distance of approximately 12 μm, with a line speed in the sample tubes 24 of approximately 2 m/s, are covered with the focus. This corresponds to a cycle in the first sample tube 24. Subsequently all other sample tubes 24 are travelled over one after the other, so that each sample tube 24 has undergone a cycle. After a waiting period of 40 s after passing through the first sample tube 24, the next cycle is started and this is repeated as often as needed until each sample tube 24 has passed through a total of 25 cycles. The starting concentration of the original 13 is selected in the first sample tube 24 to be 0 pM, in the second sample tube 24 to be 20 pM and in the third sample tube 24 to be 50 pM. For a negative control, a fourth sample tube 24 is introduced into the water bath 26, which also has the original 13 in a concentration of 50 pM, but is not covered by the laser beam. After the first, second and third sample tubes 24 have passed through 25 cycles, all four sample tubes 24 are removed from the water bath 26. To examine the effect of the laser cycles and the concentration of the original 13, a test probe 22 is used, which, under the selected buffer and hybridization conditions, can hybridize only onto the sub-sequences arising through extension of the nanoparticle-bound primers 8. The extension of the primers 8 is thereby complementary to the original 13, as shown in FIG. 6C. To produce the test probes 22, second nanoparticles 23 of gold and having a diameter of 60 nm are functionalized with oligonucleotides 4 (according to J. Hurst, see above). For one part oligonucleotide 4 ID5 and, as a filling molecule 10, in four parts oligonucleotide 4 ID2 are used. After functionalization and 6 washing steps, the second nanoparticles 23 are in a concentration of 200 pM in a PBS buffer (20 mM PBS, 10 mM NaCl, 0.01% Tween 20, 0.01% acid, 1 mM EDTA, pH 7.5). For the hybridization of the oligonucleotides 4 on the first nanoparticles 3 with the oligonucleotides 4 on the second nanoparticles 23, a modified phosphate buffer is used (13 mM PBS, 200 mM NaCl, 0.02% Tween 20, 1 mM EDTA, 20 mM sodium citrate, 1 µg/ml PVP10, pH 7.5). 10 µl hybridization formulation contains 2.25 µl of the modified phosphate buffer, 3 µl formamide, 2 µl NaCl 5M, 0.25 µl of the 200 pM test probe solution and 2.5 µl of the corresponding PCR solution from the optothermal amplification, which contains the first nanoparticles 3. If there was a sufficient amount of the original 13 with the sequence ID3 in the sample tube, on the surface of the first nanoparticles 3 the oligonucleotide 4 with the sequence ID1 is extended and can be hybridized with the oligonucleotide 4 with the sequence ID5 on the surface of the test probe 22, as shown in FIG. 6F. The detection of this hybridization is realized by means of optothermal excitation of the nanoparticles (according to EP 2162549, the related content of which is included in the present disclosure by virtue of reference thereto). The sample tubes 24 are for this purpose, as shown in FIG. 12, shot with pulses of a first laser 28 (50 µs pulse duration, 532 nm wavelength, approximately 700 mW peak power, focus diameter approximately 30 µm). The nanoparticles are hereby optothermally heated and emit heat to their environment. If first nanoparticles 3 and second nanoparticles 23 are combined through the hybridization of oligonucleotides 4, as shown in FIG. 6F, they are separated by the laser pulse. This can be detected by a second laser 29 shown in FIG. 12 (wavelength here 630 nm, power 5 mW continuously), of which the focus (30 µm diameter) is superimposed with the focus of the first laser 28, which is preferably used exclusively for de-hybridization, and which asks for the extinction before and after the laser pulse of the first laser 28. The optical path on which the extinction change is optothermally induced and measured is approximately 2 mm. The intensity of the light of the second laser 29 transmitted through this layer is measured with a photodiode 30. From the difference of the photodiode flow before and after the pulse, the optothermally induced transmission change is determined, which is produced by the de-hybridization of the extended first oligonucleotides and second oligonucleotides between the nanoparticles and the subsequent diffusing away of the nanoparticles.

Figure 8A:
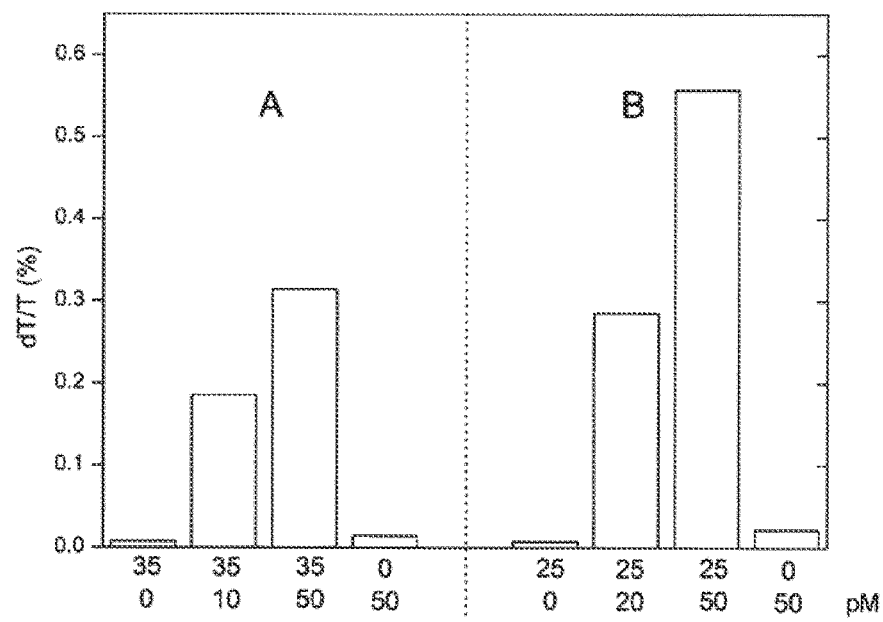
FIG. 8A shows a diagram of the relative transmission change, which is produced by the laser pulse of the first laser and the hereby arising de hybridization of the oligonucleotides between the first nanoparticles and second nanoparticles, and is a measure for the presence of gold-DNA-gold bonds in the sample tube.
Figure 8B:
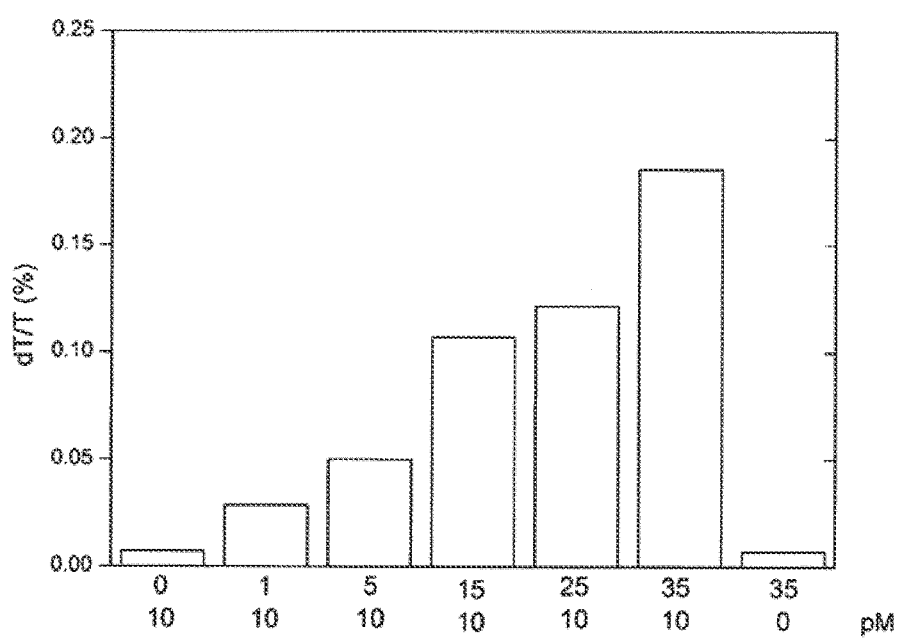
FIG. 8B shows a diagram for a similar experiment with global heating of the whole reaction volume, but with constant concentration of the original in the sample tube before the amplification.

FIG. 8A-FIG. 8B shows in two diagrams the results of amplification reactions with global and local heating with test probes for positive detection of DNA.

FIG. 8A shows the relative transmission change, which is produced by the laser pulse of the first laser 28 and the hereby arising de-hybridization of the oligonucleotides 4 between the first nanoparticles 3 and second nanoparticles 23, and is a measure for the presence of gold-DNA-gold bonds in the sample tube 24. Below the diagram in FIG. 8A, the number of cycles passed through can be seen in a first line. In a second line lying below the first line, the concentration of the original 13 in pM in the sample tube 24 before carrying out the amplification is shown. On the right side of the diagram in FIG. 8A in section B from left to right, the first, second and third sample tubes 24, each of which has passed through 25 optothermal cycles, are shown, and also the fourth sample tube 24 without optothermal treatment. It can clearly be seen here that the measured transmission change as an indicator for gold-DNA-gold bonds increases with increasing concentration of the original 13 before the amplification if the 25 cycles have been passed through. Only a slight transmission change can be observed for the first sample tube 24 without original 13 and the fourth sample tube 24 without optothermal treatment. This shows that no extension of the primer sequences 5 on the first nanoparticles 3 has taken place here and therefore no binding to the test probe 22 is possible. It is only after passing through the optothermal cycles and in the presence of the original 13 that an extension of the primer sequences 5 on the first nanoparticles 3 through the DNA polymerase 11 can arise, which leads to a combination of the first nanoparticles 3 with the second nanoparticles 23 and finally to a transmission change as a consequence of the optothermally induced separation of the nanoparticles.

By way of comparison, FIG. 8A and FIG. 8B show in Section A on the left side the result of a similar experiment, but in which the heating of the DNA is not realized locally through optothermal excitation of the nanoparticles 9, but instead globally for the whole reaction volume 2 in a conventional thermocycler (Labnet Multi Gene II). Here, the first to fourth sample tubes 24 are shown from left to right, the content of which is identical to the experiment described in the preceding paragraph. First, second and third sample tubes 24 were subjected to a conventional PCR protocol (93° C. for 1 s, 53° C. for 20 s, 35 cycles). As with the optothermal heating it can also be seen here that the more original 13 that was present in the respective sample tube 24 before the amplification, the greater is the measured transmission change, which is produced by the laser pulse and the hereby de-hybridizing DNA between the first nanoparticles 3 and second nanoparticles 23, and which is the measure for the presence of gold-DNA-gold bonds in the solution. The fourth sample tube 24, which contains 50 pM of the original 13, but was not cyclically heated, shows hardly any transmission change. Primer sequences 5 on the first nanoparticles 3 were not therefore extended to a sufficient extent.

FIG. 8B shows a similar experiment with global heating of the whole reaction volume 2, but with constant concentration of the original 13 in the sample tube 24 of 10 pM before the amplification (second line below the diagram) and increasing number of cycles (first line below the diagram). It can clearly be seen here that, with an increasing number of cycles, the measured transmission change also becomes greater, a clear sign that the more primers are extended on the first nanoparticles 3, the more cycles are passed through, and thus a clear sign that the origin of the measured signal is actually the completed extension of the oligonucleotides 4 on the first nanoparticles 3 through the DNA polymerase 11.

Figure 9A:
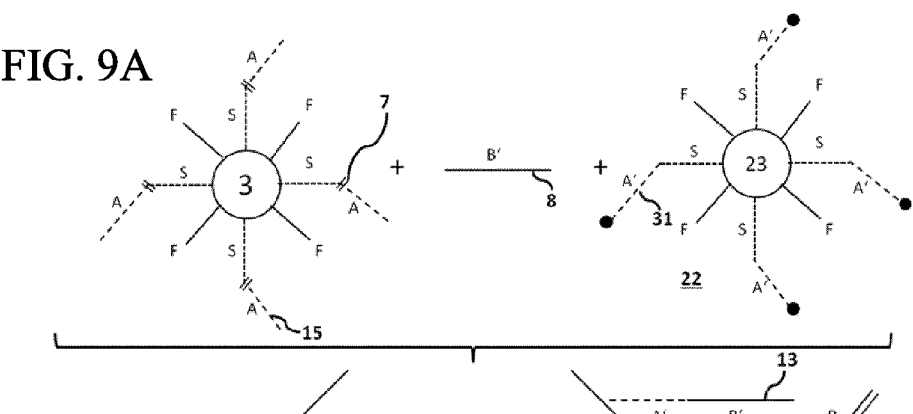
FIG. 9A shows in a schematic illustration where the spacer sequence does not have to be identical to the spacer sequence on the first nanoparticles, and an optional abasic modification between test sequence A' and spacer sequence.
Figure 9B:
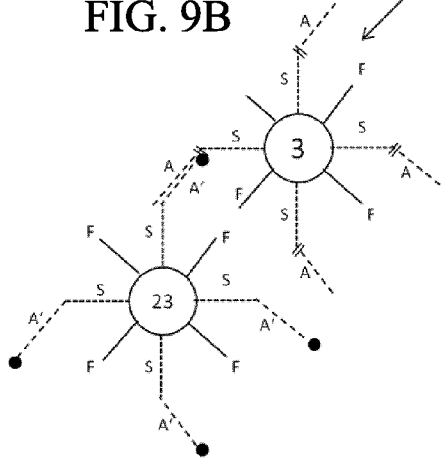
FIG. 9B shows in a schematic illustration that the first nanoparticles are combined with the second nanoparticles.
Figure 9C:
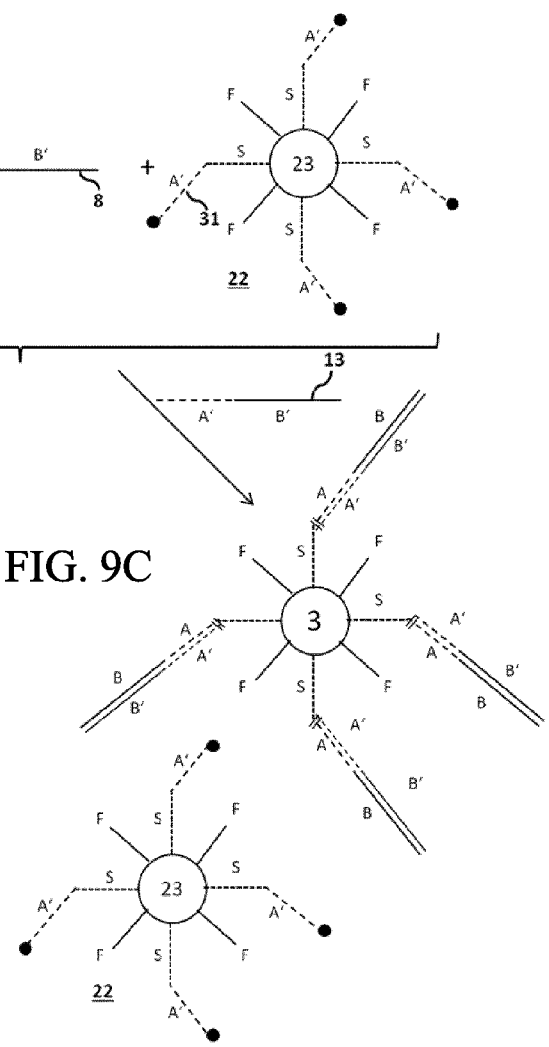
FIG. 9C shows in a schematic illustration the extended primer sequences on the first nanoparticles hybridized with the original and its copies and thus form rigid, double-stranded DNA.

FIG. 9A-FIG. 9C show in a schematic illustration the nanoparticles according to the invention and the test probes according to the invention with terminating modifications for negative detection of DNA.

A further possibility for detection of the completed amplification is shown in FIG. 9A-FIG. 9C. FIGS. 9A and 9C summarize the exponential amplification using a dissolved reverse primer 16 B', as already shown in FIGS. 1A to 1H. In addition, test probes 22 are located in the sample 12. The test probes 22 consist in this exemplary embodiment of second nanoparticles 23, which are functionalized on their surface, besides optional filling molecules 10 F, also with the test sequence 31'A. Optionally, a further spacer sequence 6 S can be between the test sequence 31 A' and the surface of the second nanoparticles 23, wherein the spacer sequence 6 S does not have to be identical to the spacer sequence 6 S on the first nanoparticles 3 of FIG. 1A-FIG. 1H or FIG. 9A, and an optional abasic modification 7 between test sequence A' and spacer sequence 6 S. The test sequence A' is complementary at least to a part of the primer sequence 5 A on the first nanoparticles 3. The test sequence A' competes with respect to the primer sequence 5 A for the copies of the original 13 formed in the method in FIGS. 1A to 1H with the sub-sequence A'. This means: if many copies of the original 13 are present, the primer sequences 5 A on the surface of the first nanoparticles 13 are then already occupied with the sub-sequences A' of the copies of the original 13. The primer sequences 5 A cannot then, or can only in a limited scope, hybridize with the test sequences A' on the second nanoparticles 23. The first nanoparticles 3 are not therefore combined with the second nanoparticles 23, or are only combined therewith to a limited extent. As shown in FIG. 9C, the extended primer sequences 5 A on the first nanoparticles 3 are hybridized with the original 13 and its copies and thus form rigid, double-stranded DNA, which can constitute a steric hindrance. A combination of first nanoparticles 3 and second nanoparticles 23 with a high number of copies of the original 13 is also thereby prevented. In the absence of, or in the case of a small number of, the original 13 and copies of the original 13, the first nanoparticles 3 are present predominantly with unoccupied primer sequences 5 A, as shown in FIG. 9B. The test sequences 31 of the test probes 22 can now hybridize with the unoccupied primer sequences 5 A on the first nanoparticles 3. The first nanoparticles 3 are thereby combined with the second nanoparticles 23, as shown in FIG. 9B. In this embodiment the degree of combination of first nanoparticles 3 and second nanoparticles 23 is weaker, the more copies of the original 13 that were produced by the amplification reaction, which in turn depends on the concentration of the original 13 at the start of the amplification reaction. The buffer and hybridization conditions (e.g. temperature, salt concentrations, nanoparticle concentrations and sizes, concentrations of other buffer additives, pH value) are selected so that, with completed specific extension of the primer sequence 5 A and completed synthesis of copies of the original 13, a prevention of the hybridization of the primer sequences 5 A with the test sequences 31 A' that is as efficient as possible takes place. At the same time the said conditions are selected so that, with incomplete amplification, a hybridization of the primer sequences 5 A with the test sequences 31 A' is produced that is as efficient as possible. The combination, resulting from the hybridization, of first nanoparticles 3 with second nanoparticles 23, can be detected, e.g., as redshift and broadening of the plasmon resonance in the extinction spectrum, or by measuring the transmission change in one or more wavelengths after optothermal excitation of the nanoparticles and resulting denaturing of the nanoparticle-bound DNA. Alternatively, the detection and quantification of the copies of the original 13 produced in the method can also be realized, e.g. by PCR, real-time PCR, quantitative real-time PCR, gel electrophoresis, or by means of colour-labelled probes. The test probes 22 can be passivated so that they do not act as primers 8. The passivation of the test probes 22 can involve the test sequence 31 on the test probes 22 being selected so that at the annealing temperature during the PCR no hybridization of the said test sequence 31 with the original 13 takes place, but instead only after subsequent reduction of the temperature. The passivation of the test probes 22 can also take place by the test sequences 31 being fixed at the 3' end on the second nanoparticles 22 so that the DNA polymerase 11 cannot extend the test sequences. In this case the test sequences 31 can be free at their 5' end or be combined with the second nanoparticles 23. The test probes 22 can also be passivated by a base modification, e.g. with dideoxy cytosine (ddC), at the 3' end of the test sequences 31 preventing extension. The test probes 22 can also be added, only after conclusion of the optothermal amplification reaction, to the sample 12.

For the embodiment of the method shown in FIG. 9A-FIG. 9C, first nanoparticles 3 of gold with a diameter of 60 nm are functionalized with oligonucleotides 4, as already in the exemplary embodiment shown in FIG. 6A-FIG. 6F, but now with oligonucleotides ID6. After functionalization and 6 washing steps, the first nanoparticles 3 are present in a concentration of 200 pM in a PBS buffer (5 mM PBS, 10 mM NaCl, 0.01% Tween 20, pH 7.5). To produce the test probes 22, second nanoparticles 23 of gold with a diameter of 10 nm are functionalized with oligonucleotides 4 ID7 (according to J. Hurst, see above), which are terminated with dideoxy cytosine (ddC) at the 3' end. After functionalisation and 6 washing steps the second nanoparticles 23 are present in a concentration of 8 nM in a PBS buffer (5 mM PBS, 10 mM NaCl, 0.01% Tween 20, pH 7.5). The amplification reaction is carried out in a total volume of 20 µl in a multiwell plate 32 with transparent bottom (supplied by Greiner Bio One) (4 µl Apta Taq Mastermix 5x with MgCl2 (obtained from Roche), 2 µl NaCl 450 mM, 2 µl MgCl2 90 mM, 2 µl Tween 20 1%, 2 µl tetramethyl ammonium chloride, 50 mM, 2 µl water, 2 µl of the functionalized first nanoparticles 200 pM, 1 µl of the functionalized second nanoparticles 8 nM, 1 µl oligonucleotide 4 ID8 as a dissolved reverse primer and 2 µl target sequence as original 13 to be amplified. The following are located in the whole volume, e.g.: 2E7, 2E6, 2E5, 2E4, 2E3, 2E2 copies of genomic DNA of the bacterium *E. coli* (*Escherischia coli*), which contains as a sub-sequence the original 13 in the sample 12, or 2E7 copies of genomic DNA of the bacterium MRSA (Methicillin-resistant *Staphylococcus aureus*), which does not contain the original 13 in the sample 12. The genomic DNA of *Escherischia coli* and MRSA was previously extracted with a commercial extraction kit (Qiagen DNeasy Blood & Tissue Kit) from *E. coli* bacteria or MRSA bacteria. The genomic DNA thus obtained was frozen for storage and heat-treated for 10 minutes at 99° C. before introduction into the amplification reaction.

Figure 10:
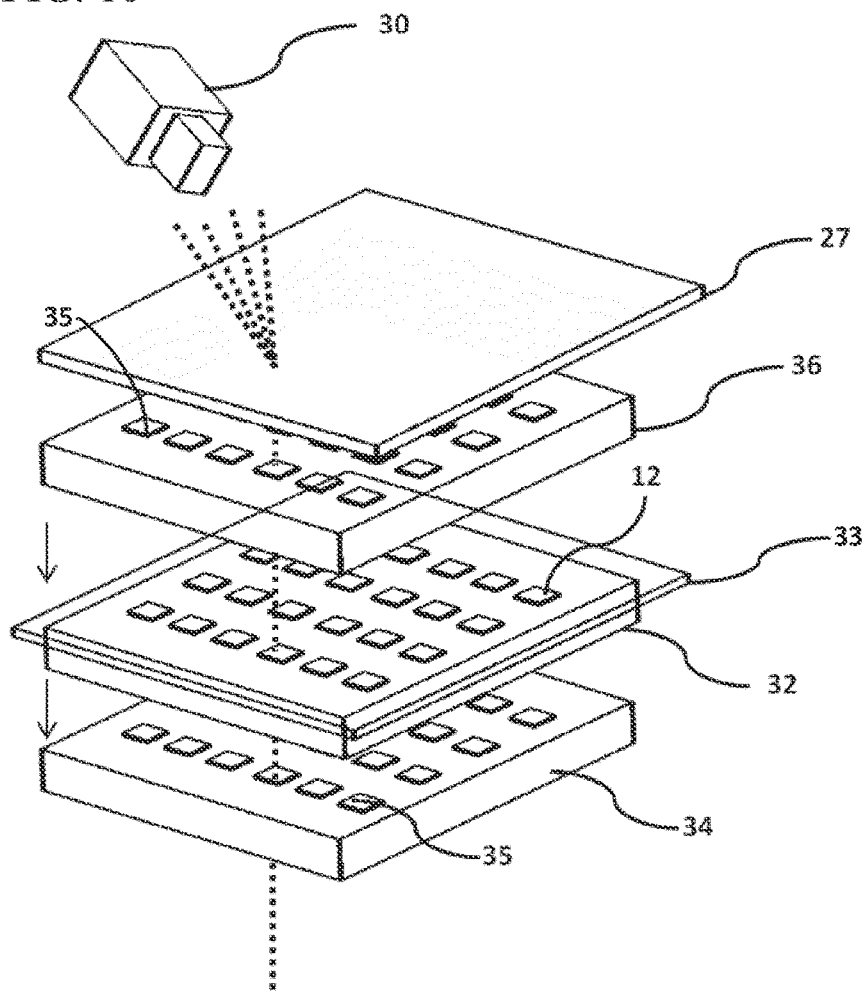
FIG. 10 shows in a schematic illustration a further structure for carrying out the method according to the invention, with a laser, two heating blocks, with recesses, multiwell plate and film as well as scattering plate and photodiode.

As shown in FIG. 10, the multiwell plate 32 is closed with a transparent film 33 (supplied by Carl Roth). The multiwell plate 32 is brought into connection from below with a first heating block 34, which has recesses 35 such that the laser 17 can reach the transparent bottom of the multiwell plate without hindrance. Through tempering of the first heating block 34 the global sample temperature can be set, which constitutes both the annealing and also the elongation temperature. The film 33 is brought into connection with a second heating block 36, which also contains recesses 35 in such a way that the laser, after crossing the sample, can propagate without hindrance. The second heating block 36 is intended to prevent a part of the sample being able to condense on the film 33. The temperature of the second heating block 36 is preferably selected to be at least as high as that of the first heating block 34, particularly preferably at least 5° C. higher, and more particularly preferably at least 10° C. higher than that of the first heating block. In the present exemplary embodiment the temperature of the first heating block is 62° C., that of the second heating block is 80° C. Under these conditions no hybridization takes place between the test sequence 24 and primer sequence 5 and therefore first nanoparticles 3 and second nanoparticles 23 are not combined with each other, and the primer sequence 5 is not blocked for the amplification reaction. With lower temperatures, which prevail, e.g. during the mixing of the reaction components, the first nanoparticles 23 and the primer sequences 5 can be partially or completely blocked by the test sequences 31 and the test probes 22 and thus be protected against non-specific bindings and hybridizations. This can be advantageous for the specificity of the amplification reaction. The laser 17 which serves to excite the nanoparticles is a frequency-doubled diode-pumped Nd:YAg laser (Excel, Laser-Quantum), which, with an output power of 1.8 W, is widened approximately 3× by means of a telescope and is then focused with a telecentric F-Theta lens (Qioptiq, focal length 100 mm) behind a mirror scanner 19 (Cambridge Technologies, Pro Series 1) into the multiwell plate 32 (focus diameter approximately 20 μm). The mirror scanner 19 allows the focus to move line by line through the multiwell plate 32, as also already shown in FIG. 3, and therefore allows the whole PCR reaction volume to take part in the optothermal amplification. For each well, 250 lines at a distance of approximately 15 μm, with a line speed in the well of approximately 8 m/s, are passed with the focus. This corresponds to one cycle in the first well. Subsequently all other wells are passed one after the other so that each well has passed through one cycle. After a waiting time of 3 s after the passage of the first well, the next cycle is started and this is repeated until each well has passed through a total of 210 cycles.

Figure 11:
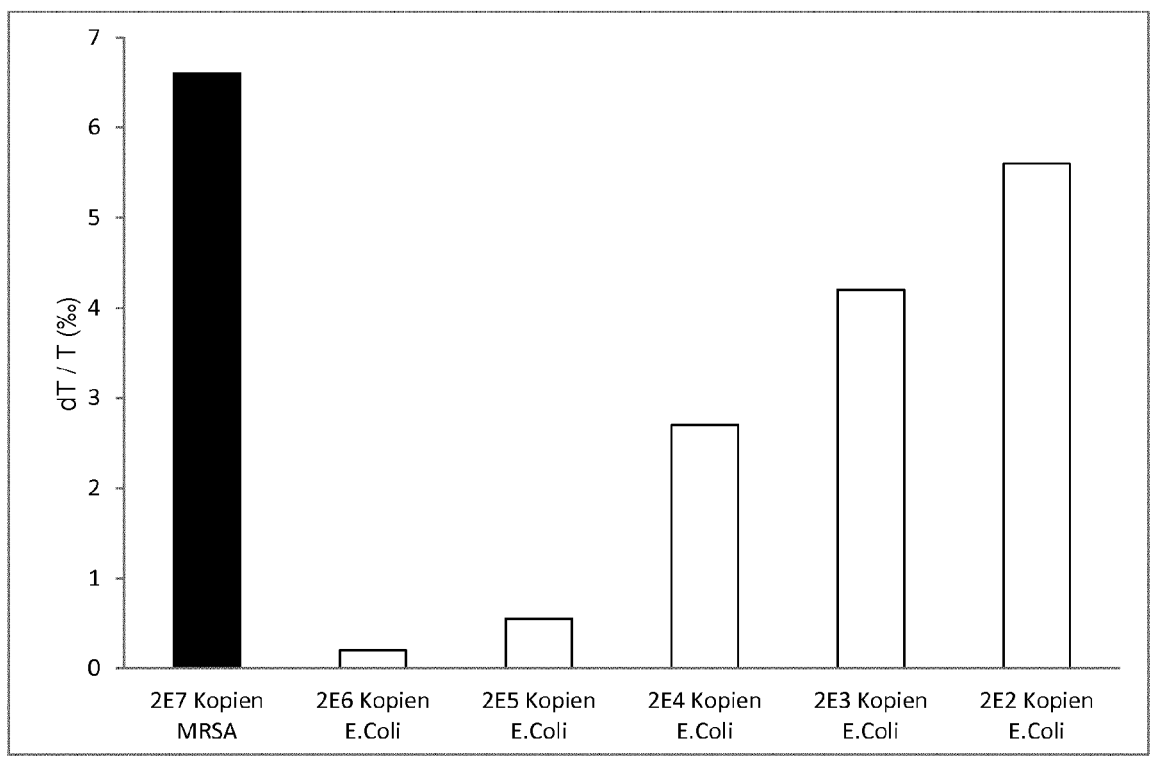
FIG. 11 shows in a diagram the results of amplification reactions with test probes for negative detection of DNA.

6 wells are examined, which are shown in FIG. 11 from left to right. The first well contains, as a control in the sample, 2E7 copies of genomic DNA of the bacterium MRSA (Methicillin-resistant *Staphylococcus aureus*), which does not contain the original 13. In the second to sixth wells the sample contains 2E7, 2E6, 2E5, 2E4, 2E3 and 2E2 copies of genomic DNA of the bacterium *E. coli*, which contains the original 13 as a sub-sequence. After all seven wells have each passed through 210 cycles and the optothermal amplification reaction has ended, the temperature of the first heating block 34 is reduced to 52° C., that of the second heating block 36 to 62° C. Under these conditions, a hybridization can take place between the test sequence 24 and primer sequence 5 if no originals 13, or only few originals 13, were present in the sample and therefore the primer sequences 5 are not blocked, or are only blocked to a small extent, by copies of the original 13. In this case, first nanoparticles 3 and second nanoparticles 23 are combined with each other, as shown in FIG. 9B. If many copies of the original 13 are present, the primer sequences 5 A on the surface of the first nanoparticles 3 are already occupied with the sub-sequences A' of the copies of the original 13. The primer sequences 5 A cannot then hybridize, or can only hybridize to a small extent, with the test sequences A' on the second nanoparticles 23. Therefore, the first nanoparticles 3 are not combined, or are only combined to a small extent, with the second nanoparticles 23. As shown in FIG. 9C, the elongated primer sequences 5 A on the first nanoparticles 3 are hybridized with the original 13 and its copies and thus form rigid, double-stranded DNA, which can constitute a steric hindrance. A combination of first nanoparticles 3 and second nanoparticles 23 is also thereby prevented in the case of a high number of copies of the original 13. The detection of the hybridization is realized by means of optothermal excitation of the nanoparticles (according to EP 2162549, the related content of which is included in the present disclosure by virtue of reference thereto). In addition, the wells are shot, as shown in FIG. 10, with pulses of a laser 17 (50 μs pulse duration, 532 nm wavelength, approximately 1 W peak power, focus diameter approximately 20 μm). The nanoparticles are hereby optothermally heated and emit heat to their environment. If first nanoparticles 3 and second nanoparticles 23 are combined through the hybridization of oligonucleotides, as shown in FIG. 9B, they are separated by the laser pulse. This can be detected in that the laser 17 asks, with a low power (approx. 50 mW continuously), for the extinction before and after the intensive laser pulse of the laser 17. The optical path on which the extinction change is optothermally induced and measured is approximately 1 mm. The low power during the extinction measurement prevents the de-hybridization of the primer sequence 5 and the test sequence 31, which is only to be induced by the intensive laser pulse. The use of only one laser both for the extinction measurement and also for the optothermal de-hybridization preferably saves costs and an overlapping of two laser foci. The intensity of the light of the laser 17 transmitted through this layer is measured with a photodiode 30 after the transmitted light of the laser 17 is scattered at a scattering plate 27. Through the scattering plate it is thereby achieved that a part of the light transmitted through the different wells always falls onto the detector. From the difference of the photodiode flow before and after the pulse, the optothermally induced transmission change is determined, which is produced through the de-hybridization of the primer sequence 5 and test sequence 24 between the nanoparticles 8 and the subsequent diffusing apart of the nanoparticles 8. The result of the optothermally induced change of the transmission is shown in FIG. 11. The first bar shows the measurement of a well with genomic DNA of the bacterium MRSA, which does not contain the original 13 as a sub-sequence in the sample. Here, the primer sequences are not occupied by copies of the original and, therefore, first nanoparticles 3 and second nanoparticles 23 combine with each other and a clear transmission change is detectable. The following bars show the measurements of the wells that contain genomic DNA of the bacterium *E. coli*, which contains the original 13 as a sub-sequence. Here, the prevention of the hybridization and thus the prevention of the transmission change is greater, the more genomic DNA of the bacterium *E. coli* that contain the original 13 as a sub-sequence in the sample 12.

The features disclosed in the above description, the claims and the drawings can be significant both individually as well as in any combination for the realisation of the invention in its different embodiments.

REFERENCE SYMBOL LIST

1 Nucleic acid
2 Reaction volume
3 First nanoparticles
4 Oligonucleotide
5 Primer sequence
6 Spacer sequence
7 Abasic modification
8 Primer
9 Nanoparticle
10 Filling molecule
11 DNA polymerase
12 Sample
13 Original
14 Complement
15 Forward primer
16 Reverse primer
17 Laser
18 Light source
19 Mirror scanner
20 Mirror 21 First oligonucleotides
22 Test probe
23 Second nanoparticles
24 Sample tube
25 Glass cuvette
26 Water bath
27 Scattering plate
28 First laser
29 Second laser
30 Photodiode
31 Test sequence
32 Multiwell plate
33 Film
34 First heating block
35 Recess
36 Second heating block

| Sequences |
|---|
| /iSp9/ = abasic modification Spacer9 |
| /ddC = dideoxy cytodine |

| Sequences |
|---|
| ID1: Thiol-5' AAAAAAAAAAAAAAAAAAAAAAAAAAAAAAAGA TAAGATAATGTAGTCCCTGGCCTCAAAG 3' |
| ID2: Thiol-5' AAAAAAAAAAAAAAAAAAAAAAAAA 3' |
| ID3: 5' ATGCAACCTAAGGAGGAGAGTTCCTTTGAGGCCAGGGACTACA TTATCTTATC 3' |
| ID4: 5' GTTGTCTTATAGCATTGGTGCCGATTTGGG 3' |
| ID5: Thiol-5' AAAAAAAAAAAAAAAAAAAAAAAAAAAAAAAAT ACAAATGCAACCTAAGGAGGAGAGTTCC 3' |
| ID6: Thiol-5' AAAAAAAAAAAAAAAAAAAAAAAAAAAAAAAA/ iSp9//iSp9/GTTCAGGCACAGCACATCA 3' |
| ID7: Thiol-5' AAAAAAAAAAAAAAAAAAAAAAAAAACTGTGC/ddC 3' |
| ID8: 5' GACGCTCACACCGATACCATCA 3' |

What is claimed is:

1. A method for amplifying nucleic acids in a sample comprising the steps of:
   (a) amplifying the nucleic acids, using a polymerase chain reaction (PCR),
      wherein a cycle of the PCR consisting of the steps of denaturing, annealing and elongation is repeated through a number of passages,
      wherein at least one of the passages of the PCR cycle comprises a cycle duration ($t_c$) that is shorter than 40 seconds,
      wherein the number of passages is greater than 60 and a duration of effect $t_A$ in at least one passage of the number of passages is less than 10 milliseconds, and
      wherein the amplification is performed using a plurality of oligonucleotides comprising at least one primer sequence and a further portion comprising a spacer sequence and at least one abasic modification selected from dideoxy-ribose, hexaethylene glycol, or triethylene glycol; and (b) testing the concentration of products of the amplification step.

2. The method of claim 1, wherein:
a global temperature of the sample during the testing step is different from a global temperature of the amplification step;
no substances are added to the sample in the testing step; and
the number of passages is greater than 60 and the duration of effect $t_A$ in at least 10 passages of the number of passages is less than 10 milliseconds.

3. The method of claim 1, wherein a global temperature of the sample during the testing step is substantially equal to a global temperature of the amplification step, and the duration of effect $t_A$ in at least one passage of the number of passages is less than 1 millisecond.

4. The method of claim 1, wherein a first nanoparticle is used in the amplification step and at least one test probe is used in the testing step, wherein each of the at least one test probes comprises a second nanoparticle.

5. The method of claim 4, wherein the second nanoparticle of the test probe has a different size from that of the first nanoparticle used in the amplification step to amplify the nucleic acids, and wherein the duration of effect $t_A$ in at least one passage of the number of passages is less than 1 nanosecond.

6. The method of claim 1, wherein the at least one primer sequence is conjugated to a first nanoparticle via the further portion and wherein the first nanoparticle transfers heat to the environment via a heating time that is shorter than 100 ms.

7. The method of claim 6, wherein the concentration of an amplicon to be amplified in the method is less than 1 pM at the start of the method.

8. The method of claim 1, wherein the number of passages is greater than 80, and the duration of effect $t_A$ in the at least one passage of the number of passages is less than 500 microseconds.

9. The method of claim 1, wherein the number of passages is greater than 100, and the duration of effect $t_A$ in the at least one passage of the number of passages is less than 100 microseconds.

10. The method of claim 1, wherein:
the amplification step comprises a first nanoparticle conjugated to the at least one oligonucleotide comprising the at least one primer sequence, the spacer sequence, and the at least one abasic modification, and wherein the at least one abasic modification is between the spacer sequence and the primer sequence, and the spacer sequence is bound to the first nanoparticle; and
the testing step comprises a second nanoparticle conjugated to at least one test probe, and wherein the second nanoparticle is smaller than the first nanoparticles.

11. The method of claim 10, comprising providing the second nanoparticles to the sample before or during the amplification step, wherein the number of passages is greater than 60 and the duration of effect $t_A$ in at least 20 passages of the number of passages is less than 10 milliseconds, and wherein the at least one abasic modification comprises a plurality of abasic modifications.

12. The method of claim 11, the method further comprising providing different local temperatures around the first nanoparticles and around the second nanoparticles during the amplification step.

13. The method of claim 1, wherein the amplification step overlaps with the testing step.

14. A method for amplifying nucleic acids in a sample comprising the steps of:
amplifying the nucleic acids, wherein the amplification is performed by a polymerase chain reaction, wherein:
a cycle of the polymerase chain reaction consisting of the steps of denaturing, annealing and elongation is repeated through a number of passages, and wherein the number of passages is greater than 60 and a duration of effect $t_A$ in at least one passage of the number of passages is less than 10 milliseconds;
a first nanoparticle is conjugated to at least one oligonucleotide comprising at least one primer sequence and a further portion comprising a spacer sequence bound to the first nanoparticle and at least one abasic modification, wherein the at least one abasic modification is located between the spacer sequence and the primer sequence; and
testing the concentration of products of the amplification step, wherein the testing step comprises a second nanoparticle conjugated to at least one test probe, wherein the second nanoparticle is smaller than the first nanoparticle, and wherein the testing step begins after the end of the amplification step, and substances are added at least to a part of the sample in the testing step.

15. The method of claim 14, wherein the further portion extends from the nanoparticle-proximal end of the primer sequence in the direction of the first nanoparticle, and the further portion comprises at least one abasic modification selected from dideoxy-ribose and triethylene glycol.

16. The method of claim 15, wherein at least 50% of a global temperature of the sample during the testing step is different from a global temperature of the amplification step, and wherein the at least one abasic modification is triethylene glycol.

17. The method of claim 14, wherein amplifying the nucleic acids and testing the concentration of the products comprises transferring heat to the first nanoparticle and the second nanoparticle to heat the sample at different global temperatures during testing step and the amplification step using a first heating block brought in connection with a bottom of a plate containing the sample and a second heating block brought in connection with a film on top of the plate, and wherein the duration of effect to in at least 10 passages of the number of passages is less than 10 microseconds.

18. A method for amplifying nucleic acids in a sample comprising the steps of:
amplifying the nucleic acids, wherein the amplification is performed by a polymerase chain reaction and using a plurality of oligonucleotides that have at least one primer sequence and a further portion, wherein the further portion comprises a spacer sequence and at least one abasic modification comprising triethylene glycol between the spacer sequence and the primer sequence, wherein:
the spacer sequence provides space for the nucleic acids to access the at least one primer sequence for the amplification;
a cycle of the polymerase chain reaction consisting of the steps of denaturing, annealing and elongation is repeated through a number of passages, and wherein the number of passages is greater than 60 and a duration of effect $t_A$ in at least one passage of the number of passages is less than 10 milliseconds, and wherein at least one of the passages of the PCR cycle comprises a cycle duration ($t_c$) that is shorter than 40 seconds; and testing the concentration of products of the amplification step.

* * * * *

SEQUENCE LISTING

<160> NUMBER OF SEQ ID NOS: 8

<210> SEQ ID NO 1
<211> LENGTH: 65
<212> TYPE: DNA
<213> ORGANISM: Artificial Sequence
<220> FEATURE:
<223> OTHER INFORMATION: ID1; with 5' Thiol modification

<400> SEQUENCE: 1
aaaaaaaaaa aaaaaaaaaa aaaaaaaaaa aaaaagataa gataatgtag tccctggcct    60
caaag                                                                65

<210> SEQ ID NO 2
<211> LENGTH: 25
<212> TYPE: DNA
<213> ORGANISM: Artificial Sequence
<220> FEATURE:
<223> OTHER INFORMATION: ID2; with 5' Thiol modification

<400> SEQUENCE: 2
aaaaaaaaaa aaaaaaaaaa aaaaa                                          25

<210> SEQ ID NO 3
<211> LENGTH: 53
<212> TYPE: DNA
<213> ORGANISM: Artificial Sequence
<220> FEATURE:
<223> OTHER INFORMATION: ID3; engineered sequence

<400> SEQUENCE: 3
atgcaaccta aggaggagag ttcctttgag gccagggact acattatctt atc           53

<210> SEQ ID NO 4
<211> LENGTH: 30
<212> TYPE: DNA
<213> ORGANISM: Artificial Sequence
<220> FEATURE:
<223> OTHER INFORMATION: ID4; engineered sequence

```
<400> SEQUENCE: 4
gttgtcttat agcattggtg ccgatttggg                                      30

<210> SEQ ID NO 5
<211> LENGTH: 65
<212> TYPE: DNA
<213> ORGANISM: Artificial Sequence
<220> FEATURE:
<223> OTHER INFORMATION: ID5; wth 5' Thiol modification

<400> SEQUENCE: 5
aaaaaaaaaa aaaaaaaaaa aaaaaaaaaa aaaaaataca aatgcaacct aaggaggaga    60
gttcc                                                                65

<210> SEQ ID NO 6
<211> LENGTH: 56
<212> TYPE: DNA
<213> ORGANISM: Artificial Sequence
<220> FEATURE:
<223> OTHER INFORMATION: ID6; with 5' Thiol modification
<220> FEATURE:
<221> NAME/KEY: misc_feature
<222> LOCATION: (36)..(36)
<223> OTHER INFORMATION: abasic modification Spacer9
<220> FEATURE:
<221> NAME/KEY: misc_feature
<222> LOCATION: (37)..(37)
<223> OTHER INFORMATION: abasic modification Spacer9

<400> SEQUENCE: 6
aaaaaaaaaa aaaaaaaaaa aaaaaaaaaa aaaaanngtt caggcacagc acatca        56

<210> SEQ ID NO 7
<211> LENGTH: 33
<212> TYPE: DNA
<213> ORGANISM: Artificial Sequence
<220> FEATURE:
<223> OTHER INFORMATION: ID7; with 5' Thiol modification
<220> FEATURE:
<221> NAME/KEY: misc_feature
<222> LOCATION: (33)..(33)
<223> OTHER INFORMATION: n is Dideoxycytidine

<400> SEQUENCE: 7
aaaaaaaaaa aaaaaaaaaa aaaaaactgt gcn                                  33

<210> SEQ ID NO 8
<211> LENGTH: 22
<212> TYPE: DNA
<213> ORGANISM: Artificial Sequence
<220> FEATURE:
<223> OTHER INFORMATION: ID8; engineered sequence

<400> SEQUENCE: 8
gacgctcaca ccgataccat ca                                              22
```